(12) United States Patent
Kusakabe

(10) Patent No.: US 8,082,131 B2
(45) Date of Patent: Dec. 20, 2011

(54) ELECTRONIC STATE CALCULATION METHOD, ELECTRONIC STATE CALCULATION DEVICE, COMPUTER PROGRAM, AND RECORDING MEDIUM

(75) Inventor: Koichi Kusakabe, Suita (JP)

(73) Assignee: Osaka University, Suita (JP)

( * ) Notice: Subject to any disclaimer, the term of this patent is extended or adjusted under 35 U.S.C. 154(b) by 390 days.

(21) Appl. No.: 12/227,789

(22) PCT Filed: Mar. 2, 2007

(86) PCT No.: PCT/JP2007/054057
§ 371 (c)(1),
(2), (4) Date: Nov. 26, 2008

(87) PCT Pub. No.: WO2007/141942
PCT Pub. Date: Dec. 13, 2007

(65) Prior Publication Data
US 2009/0093973 A1 Apr. 9, 2009

(30) Foreign Application Priority Data
May 29, 2006 (JP) .................................. 2006-148978

(51) Int. Cl.
*G06F 17/10* (2006.01)
(52) U.S. Cl. ............................................. 703/2; 703/13
(58) Field of Classification Search .................. 703/2, 5, 703/13
See application file for complete search history.

(56) References Cited

U.S. PATENT DOCUMENTS
6,185,472 B1 * 2/2001 Onga et al. .................... 700/121
2007/0198235 A1 * 8/2007 Takeuchi ........................... 703/2

OTHER PUBLICATIONS

Kohn et al., "Self-Consistent Equations Including Exchange and Correlation Effects", Physics Review, vol. 140, No. 4A, Nov. 1965, pp. A1133-A1138.*
Schluter et al., "Density Functional Theory", Physics Today, Feb. 1982, pp. 36-43.*
Rafii-Tabar, "Computational modeling of Thermo-Mechanical and Transport Properties of Carbon Nanotubes", Physics Reports, vol. 390, 2004, pp. 235-452.*
Keisanki Material Design Nyumon (Approach to calculator material design), edited by H. Kasai, Hisazumi Akai, Hiroshi Yoshida, Osaka University Press, 2005, pp. 190-216 and 378-391.
Meeting Abstracts of the Physical Society of Japan, vol. 61, Issue 1 (61st Annual Meeting), Pt. 2, Mar. 4, 2006.

(Continued)

*Primary Examiner* — Kamini S Shah
*Assistant Examiner* — Herng-Der Day
(74) *Attorney, Agent, or Firm* — Edwards Wildman Palmer LLP; Peter C. Schechter; George N. Chaclas

(57) ABSTRACT

By receiving input of a crystal structure and atom numbers, and specifying an atom group that can generate fluctuations from an electronic state calculation of a normal Kohn-Sham theory, an electronic state calculation device calculates a reference system. Next, based on an extended Kohn-Sham theory, the electronic state calculation device performs self-consistent calculation for an effective many-body system, then determines whether or not density fluctuations obtained for the reference system and density fluctuations obtained by the self-consistent calculation coincide with each other, and in a case of coincidence, acquires parameters of an exchange correlation energy and a local interaction. By the acquired parameters, an effective Hamiltonian is decided, and optimization of an electronic state is performed for a known crystal structure.

17 Claims, 10 Drawing Sheets

OTHER PUBLICATIONS

A Uniqueness Theorem in a Desnity-matrix Functional Theory, K. Kusakabe, May 29, 2005.

A First-Principles Calculational Method for the Magnetic Impurity Problem Based on a Density-Matrix Functional Theory, K. Kusakabe, et al., Physica B, publised by Elsevier, B.V., 2006.

A Uniqueness Theorem in a Density-Matrix Functional Theory, K. Kusakabe, Sep. 28, 2005.

Bulletin of the American Physical Society, Mar. 2005 Meeting Edition, vol. 50, No. 1, Mar. 21-25, 2005.

Suiso Bunshi ni okeru Kyokusho Sokan no Energy Hankansu Izonsei, H. Takahashi et al., The Physical Society of Japan Koen Gaiyoshu, vol. 61, No. 1, p. 331, Mar. 4, 2006.

Zairyo Kenkyuyo Daiichi Genri Keisan Program Mixed Basis no Shokai, T. Adachi et al., Hitachi TO Giho, No. 9, p. 77-83, Dec. 12, 2003.

Suri Model no Kakutoku Keisan Busshitsu Kagaku: Ryoshiron ni Motozuku Simulation, J. Oshiyama, Journal of the Society of Instrument and Control Engineers, vol. 41, No. 12, p. 875-880, Dec. 10, 2002.

Daikibo Keisanki Simulation Tokushugo Daikibo Keisanki Simulation ni yoru Material Design, H. Akai, System/Seigyo/Joho, vol. 48, No. 7, p. 14-18, Jul. 15, 2004.

International Search Report, May 15, 2007, issued in PCT/JP2007/054057.

PCT Request, PCT/RO/101, see p. 3.

Meeting Abstracts of the Physical Society of Japan, vol. 61, Issue 1 (61st Annual Meeting), Pt. 2, Mar. 4, 2006 With partial English Translation.

A self-consistent first-principles calculation scheme for correlated electron systems, K. Kusakabe et al.; Oct. 18, 2007.

A New Framework of the Density Functional Theory, K. Kusakabe; Feb. 1, 2007.

\* cited by examiner

ELECTRONIC STATE CALCULATION METHOD, ELECTRONIC STATE CALCULATION DEVICE, COMPUTER PROGRAM, AND RECORDING MEDIUM

This application is the national phase under 35 U.S.C. §371 of PCT International Application No. PCT/JP2007/054057 which has an International filing date of Mar. 2, 2007 and designated the United States of America.

BACKGROUND

1. Technical Field

The present invention relates to an electronic state calculation method, an electronic state calculation device, and a computer program capable of calculating an electronic state of a substance by a first-principle calculation, and a recording medium in which the computer program is recorded.

2. Description of Related Art

Conventionally, among a method called a first-principle calculation theory of estimating a physical or chemical properties (called properties hereinafter) of a substance according to a basic rule of quantum mechanics, a first-principle electronic state calculation theory based on a density functional theory is known, in which by exactly realizing reproduction of total energy and one-electron density, properties such as mechanical properties including elasticity, conductive properties including superconductive properties, a dielectric property, and a magnetic property, are reproduced with relatively high accuracy, and a calculation scale is settled in an implementable range. This calculation theory is already applied to design of a substance, and there exist a plurality of examples with its estimation accuracy verified through experiments (for example, see "Keisanki Material Design Nyumon (Approach to calculator material design)" edited by Hideaki Kasai, Hisazumi Akai, Hiroshi Yoshida, Osaka University Press (2005)).

SUMMARY

Conventionally, calculation is usually conducted by introducing an auxiliary equation of an independent particle system called a Kohn-Sham equation. However, reproducibility is not ensured for physical quantities other than a total energy and one-electron density, and a problem as described below has been pointed out.

First, there is a problem that an excitation energy given by the Kohn-Sham equation itself does not necessarily provide electrons/holes excitation of the original substance system and it is so decided that there is no gap in the substance that originally has a charge gap.

In addition, even in a case of using an extension with electron density and spin density (or four current density) set as order variables, it is only possible to obtain a solution of an independent fermion system as a reference system, and when superconductivity and orbital order formation provided by a magnetic property and a strong correlation effect are discussed, the expression itself is incomplete, and therefore it is so considered that there is a limit in the reproducibility of properties. Note that an approximate form of an exchange-correlation energy functional is further necessary for practical application of the Kohn-Sham equation, and usually Local Density Approximation (LDA) and a generalized gradient approximation (GGA) have been employed.

The present invention was made in view of the above-described circumstances, and an object of the present invention is to provide an electronic state calculation method, an electronic state calculation device, a computer program, and a recording medium capable of obtaining physical quantities other than a total energy and one-electron density and, for example, dielectric response, magnetic permeability, a reaction process of a system, and dynamics, by deciding a model to reproduce fluctuations in the physical quantities characterizing a substance, and obtaining the electronic state by a first-principle calculation with the decided model set as an initial condition.

An electronic state calculation method according to the first invention is characterized in that the method for calculating an electronic state of a substance by a first-principle calculation comprises the steps of deciding a model to reproduce fluctuations of physical quantities characterizing physical properties of the substance and obtaining the electronic state of the substance by the first-principle calculation with the decided model set as an initial condition.

According to a first aspect of the invention, a model for reproducing fluctuations in physical quantities characterizing properties of a substance is decided, and an electronic state is obtained by a first-principle calculation with the decided model set as an initial condition. Accordingly, when a model capable of simultaneously reproducing the fluctuations in the physical quantities, the model being capable of giving energy and one-electron density equivalent to a Schrödinger equation of an electron system showing a ground state without degeneracy, can be given as a functional regarding a wave function by using a universal energy functional, then a parameter inherent in the model is uniquely defined.

The electronic state calculation method according to the second invention is characterized in that the electronic state is obtained by using an optimization method based on an extended Kohn-Sham theory formulated by an expression including a residual exchange correlation energy functional expressed by the following equation.

$$E_{rxc}[n_\psi] = E_{xc}[n_\psi] + \min_{\Phi \to n_\Psi} \langle \Phi|T|\Phi \rangle - \min_{\Psi' \to n_\Psi} \langle \Psi'|T + V_{red}|\Psi' \rangle \quad \text{[Equation 1]}$$

Wherein $n_\Psi$ indicates one-electron density, $E_{xc}[n_\Psi]$ indicates an exchange correlation energy functional, $\Phi$ indicates a many-particle wave function in a state in which correlation is not generated, $\Psi'$ indicates a many-particle wave function in a state in which the correlation is generated, T indicates a kinetic energy operator, and $V_{red}$ indicates an operator defined by the following correlation function given by a set of physical quantities $\{X_i\}$.

$$\langle \Psi|V_{red}|\Psi \rangle = \sum_i W_i \langle \Psi|(X_i - \overline{X}_i) \cdot (X_i - \overline{X}_i)|\Psi \rangle \quad \text{[Equation 2]}$$

Wherein i=1, 2, 3, ..., N (N is the number of physical quantities to be calculated), $W_i$ indicates a parameter expressing a weight, and a symbol in a small parenthesis indicates a difference between the physical quantities $X_i$ and a mean value of the physical quantities $X_i$.

According to a second aspect of the invention, in an extended Kohn-Sham equation, residual exchange correlation energy is expressed as a normal exchange correlation energy and a difference therefrom, by an identity transformation from an exact expression. This differential part is given as the difference of a kinetic energy and an expected value (fluctuations) Of $V_{red}$, between two states of a state in which there are fluctuations to reproduce the same electron density and a state in which there are no fluctuations. Then variation in this kinetic energy is given in the frame of an extended Kohn-Sham theory, whereby calculation of the electronic state is possible without using a highly accurate calculation method such as a Quantum Monte Carlo Method and a Configuration Interaction Method.

The electronic state calculation method according to the third invention is characterized in that by changing a magnitude of the fluctuations with effective interaction between electrons made variable, evaluation of a kinetic energy and a total energy is performed in two states of a state in which there are fluctuations to reproduce the same electron density and a state in which there are no fluctuations.

According to a third aspect of the invention, by evaluating the kinetic energy and the total energy in two states of a state in which there are the fluctuations to reproduce the same electron density and a state in which there are no fluctuations, the calculation of the electronic state is possible in the frame of the extended Kohn-Sham equation.

The electronic state calculation method according to the fourth invention is characterized in that when the model is decided, fluctuations with respect to the physical quantities are calculated by using a calculation technique of a many-body electron system, and fluctuations with respect to the physical quantities are calculated based on an extended Kohn-Sham theory including an exchange correlation potential and Coulomb interaction between electrons, and parameters describing the model are decided such that the obtained two fluctuations are approximately equal to each other.

According to a fourth aspect of the invention, in order to decide a model so that the fluctuations of the physical quantities calculated as a reference system can be reproduced, a wave function of a many-body system is obtained by using a parameter defined in the process of deciding this model.

The electronic state calculation method according to the fifth invention is characterized in that the extended Kohn-Sham theory is formulated as an optimization problem of a wave function functional expressed by the following equation.

$$G_{Wi}[\Psi] = \langle \Psi | T + V_{red} | \Psi \rangle - \min_{\Psi' \to n_\Psi} \langle \Psi' | T + V_{red} | \Psi' \rangle + F[n_\Psi] + \int d^3 r v_{ext}(r) n_\Psi(r)$$ [Equation 3]

Wherein $\Psi$ indicates a many-particle wave function, T indicates a kinetic energy operator, $n_\Psi$ indicates one-electron density, F[n] indicates a universal energy functional, $\Psi'$ indicates a many-particle wave function minimizing $<T+V_{red}>$ with a condition that one electron density $n_\Psi$ is reproduced, $v_{ext}$ indicates an external interaction potential, and $V_{red}$ indicates an operator defined by the equation 2.

According to a fifth aspect of the invention, a ground state energy of a Coulomb system and its one-particle density are given by an optimization problem of a wave function functional expressed by equation 3.

The electronic state calculation method according to the sixth invention is characterized in that the parameter includes a parameter regarding an exchange correlation energy and local interaction between electrons.

According to a sixth aspect of the invention, definition of an effective potential is possible, which is given by applying density variation to Legendre transformation of the energy functional including an exchange energy and a correlation energy. Therefore, in an effective integral Hamiltonian composed of a kinetic energy portion of Hamiltonian and this effective potential, it is possible to obtain an expression that an interacted virtual electron system is moved.

The electronic state calculation method according to the seventh invention is characterized in that the calculation technique includes a Quantum Monte Carlo Method, a Transcorrelated Method, a Configuration Interaction Method, a Perturbational calculation/Green's function Method, or an Effective Potential Method.

According to a seventh aspect of the invention, when density/density correlation of a many-body electron system is obtained as a reference system, the Quantum Monte Carlo Method, the Transcorrelated Method, the Configuration Interaction Method, the Perturbational Calculation/Green's function method, or the effective potential method are used.

The electronic state calculation method according to the seventh invention is characterized in that a plane wave basis expansion method, a reinforced plane wave basis expansion method, an actual space, a numerical basis expansion method, a mixed basis expansion method, a localized basis expansion method, or a linear MT orbital method are used for the calculation of a correlation function based on the extended Kohn-Sham theory.

According to an eighth aspect of the invention, when the correlation function is obtained based on the extended Kohn-Sham equation, the plane wave basis expansion method, the reinforced plane wave basis expansion method, the actual space, the numerical value basis expansion method, the mixed basis expansion method, the localized basis expansion method, or the linear MT orbital method are used.

The electronic state calculation method according to the ninth invention is characterized in that the fluctuations are described by two-dimensional correlation function having a positive definite and a bounded value range.

According to a ninth aspect of the invention, the fluctuations of the physical quantities are described by a two-dimensional correlation function having a positive definite and a bounded value range. Therefore, when a model capable of simultaneously reproducing the correlation function with bounded positive definite, the model being capable of giving energy and one-electron density equivalent to a Schrödinger Equation of an electron system showing a ground state without degeneracy, can be given by using a universal energy functional, then a parameter inherent in the model is uniquely defined.

The electronic state calculation method according to the tenth invention is characterized in that the physical quantities are quantities described by numerical operators or generation/annihilation operators regarding electrons in a localized orbital.

According to a tenth aspect of the invention, the physical quantities are described as numerical operators or generation/annihilation operators regarding electrons in a localized orbital, and therefore the corresponding extended Kohn-Sham model is obtained as a strong correlation electron model including a first principle impurity Anderson Model and a first principle Hubbard model.

The electronic state calculation method according to the eleventh invention is characterized in that the physical quantities are physical quantities deciding a structural factor, an optical response coefficient, or a dielectric constant, magnetic permeability, electric conductivity, or elasticity of the substance.

According to an eleventh aspect of the invention, by deciding a model to reproduce the fluctuations of the physical quantities, a structural factor of a substance (namely atomic arrangement in an atomic level) is defined, and therefore all other physical quantities are defined with no contradiction and without a prerequisite.

An electronic state calculation device according to the twelfth invention is characterized in that the device that calculates an electronic state of a substance by a first-principle calculation, comprises means for deciding a model to reproduce fluctuations of physical quantities characterizing physical properties of the substance and means for obtaining the electronic state of the substance by the first-principle calculation with the decided model set as an initial condition.

According to a twelfth aspect of the invention, a model for reproducing fluctuations in physical quantities characterizing properties of a substance is decided, and an electronic state is obtained by a first-principle calculation with the decided model set as an initial condition. Accordingly, when a model capable of simultaneously reproducing the fluctuations in the physical quantities, the model being capable of giving energy and one-electron density equivalent to a Schrödinger equation of an electron system showing a ground state without degeneracy, can be given as a functional regarding a wave function by using a universal energy functional, then a parameter inherent in the model is uniquely defined.

The electronic state calculation device according to the thirteenth invention is characterized in that the electronic state is obtained by using an optimization technique based on an extended Kohn-Sham theory formulated by an expression including a residual exchange correlation energy functional expressed by the following equation.

$$E_{rxc}[n_\psi] = E_{xc}[n_\phi] + \min_{\Phi \to n_\psi} \langle \Phi|T|\Phi \rangle - \min_{\Psi' \to n_\psi} \langle \Psi'|T + V_{red}|\Psi' \rangle \quad \text{[Equation 4]}$$

Wherein $n_\Psi$ indicates one-electron density, $E_{xc}[n_\Psi]$ indicates an exchange correlation energy functional, $\Phi$ indicates a many-particle wave function in a state in which correlation is not generated, $\Psi'$ indicates a many-particle wave function in a state in which the correlation is generated, T indicates a kinetic energy operator, and $V_{red}$ indicates an operator defined by the following correlation function given by a set of physical quantities $\{X_i\}$.

$$\langle \Psi|V_{red}|\Psi \rangle = \sum_i W_i \langle \Psi|(X_i - \bar{X}_i) \cdot (X_i - \bar{X}_i)|\Psi \rangle \quad \text{[Equation 5]}$$

Wherein i=1, 2, 3, . . . , N (N is the number of physical quantities to be calculated), $W_i$ indicates a parameter expressing a weight, and a symbol in a small parenthesis indicates a difference between the physical quantities $X_i$ and a mean value of the physical quantities $X_i$.

According to a thirteenth aspect of the invention, in an extended Kohn-Sham equation, residual exchange correlation energy is expressed as a normal exchange correlation energy and a difference therefrom, by an identity transformation from an exact expression. This differential part is given as the difference of a kinetic energy and an expected value of $V_{red}$, between two states of a state in which there are fluctuations to reproduce the same electron density and a state in which there are no fluctuations. Then variation in this kinetic energy is given in the frame of an extended Kohn-Sham theory, whereby calculation of the electronic state is possible without using a highly accurate calculation method such as a Quantum Monte Carlo Method and a Configuration Interaction Method.

The electronic state calculation device according to the fourteenth invention is characterized in that the device comprises means for evaluating a kinetic energy and a total energy in two states of a state in which there are fluctuations to reproduce the same electron density and a state in which there are no fluctuations, by changing a magnitude of the fluctuations with effective interaction between electrons made variable.

According to a fourteenth aspect of the invention, by evaluating the kinetic energy and the total energy in two states of a state in which there are the fluctuations to reproduce the same electron density and a state in which there are no fluctuations, the calculation of the electronic state is possible in the frame of the extended Kohn-Sham equation.

The electronic state calculation device according to the fifteenth invention is characterized in that the device comprises means for calculating fluctuations with respect to the physical quantities by using a calculation technique of a many-body system, means for calculating fluctuations with respect to the physical quantities based on an extended Kohn-Sham theory including an exchange correlation potential and Coulomb interaction between electrons, and means for deciding parameters describing the model such that the obtained two fluctuations are approximately equal to each other.

According to a fifteenth aspect of the invention, in order to decide a model so that the fluctuations of the physical quantities calculated as a reference system can be reproduced, a wave function of a many-body system is obtained by using a parameter defined in the process of deciding this model.

The electronic state calculation device according to the sixteenth invention is characterized in that the extended Kohn-Sham theory is formulated as an optimization problem of a wave function functional expressed by the following equation.

$$G_{Wi}[\Psi] = \langle \Psi|T + V_{red}|\Psi \rangle - \min_{\Psi' \to n_\Psi} \langle \Psi'|T + V_{red}|\Psi' \rangle + F[n_\Psi] + \int d^3 r v_{ext}(r) n_\Psi(r) \quad \text{[Equation 6]}$$

Wherein $\Psi$ indicates a many-particle wave function, T indicates a kinetic energy operator, $n_\Psi$ indicates one-electron density, F[n] indicates a universal energy functional, $\Psi'$ indicates a many-particle wave function minimizing $\langle T+V_{red} \rangle$ with a condition that one electron density $n_\Psi$ is reproduced, $v_{etx}$ indicates an external interaction potential, and $V_{red}$ indicates an operator defined by the equation 5.

According to a fifth aspect of the invention, a ground state energy of a Coulomb system and its one-particle density are given by an optimization problem of a wave function functional expressed by equation 6.

A computer program according to the seventeenth invention is characterized in that the computer program for causing a computer to calculate an electronic state of a substance by a first-principle calculation, comprises a first step of deciding a model to reproduce fluctuations of physical quantities characterizing physical properties of the substance; and a second step of causing the computer to calculate the electronic state of the substance by the first-principle calculation with the decided model set as an initial condition.

According to a seventeenth aspect of the invention, a model for reproducing fluctuations in physical quantities characterizing properties of a substance is decided, and an electronic state is obtained by a first-principle calculation with the decided model set as an initial condition. Accordingly, when a model capable of simultaneously reproducing the fluctuations in the physical quantities, the model being capable of giving energy and one-electron density equivalent to a Schrödinger equation of an electron system showing a ground state without degeneracy, can be given as a functional regarding a wave function by using a universal energy functional, then a parameter inherent in the model is uniquely defined.

The computer program according to the eighteenth invention is characterized in that an optimization technique based on an extended Kohn-Sham theory formulated by an expression including a residual exchange correlation energy functional expressed by the following equation, as the first first-principle calculation.

$$E_{rxc}[n_\psi] = E_{xc}[n_\phi] + \min_{\Phi \to n_\psi} \langle \Phi|T|\Phi \rangle - \min_{\Psi' \to n_\psi} \langle \Psi'|T + V_{red}|\Psi' \rangle \quad \text{[Equation 7]}$$

Wherein $n_\psi$ indicates one-electron density, $E_{xc}[n_\psi]$ indicates an exchange correlation energy functional, $\Phi$ indicates a many-particle wave function in a state in which no correlation is generated, $\Psi'$ indicates a many-particle wave function in a state in which the correlation is generated, T indicates a kinetic energy operator, and $V_{red}$ indicates an operator defined by the following correlation function given by a set of physical quantities $\{X_i\}$.

$$\langle \Psi|V_{red}|\Psi \rangle = \sum_i W_i \langle \Psi|(X_i - \overline{X}_i) \cdot (X_i - \overline{X}_i)|\Psi \rangle \quad \text{[Equation 8]}$$

Wherein $i=1, 2, 3, \ldots, N$ (N is the number of the physical quantities to be calculated), $W_i$ indicates a parameter expressing a weight, and a symbol in a small parenthesis indicates a difference between the physical quantities $X_i$ and a mean value of the physical quantities $X_i$.

According to an eighteenth aspect of the invention, in an extended Kohn-Sham equation, residual exchange correlation energy is expressed as a normal exchange correlation energy and a difference therefrom, by an identity transformation from an exact expression. This differential part is given as the difference of a kinetic energy and an expected value Of $V_{red}$, between two states of a state in which there are fluctuations to reproduce the same electron density and a state in which there are no fluctuations. Then variation in this kinetic energy is given in the frame of an extended Kohn-Sham theory, whereby calculation of the electronic state is possible without using a highly accurate calculation method such as a Quantum Monte Carlo Method and a Configuration Interaction Method.

The computer program according to the nineteenth invention is characterized in that the computer program comprises the steps of causing a computer to change a magnitude of the fluctuations with effective interaction between electrons made variable and causing the computer to evaluate a kinetic energy and a total energy in two states of a state in which there are the fluctuations to reproduce the same electron density and a state in which there are no fluctuations.

According to a nineteenth aspect of the invention, by evaluating the kinetic energy and the total energy in two states of a state in which there are the fluctuations to reproduce the same electron density and a state in which there are no fluctuations, the calculation of the electronic state is possible in the frame of the extended Kohn-Sham equation.

The computer program according to the twentieth invention is characterized in that the first step includes the steps of: causing the computer to calculate fluctuations with respect to the physical quantities by using a calculation technique of a many-body electron system; causing the computer to calculate fluctuations with respect to the physical quantities based on an extended Kohn-Sham theory including an exchange correlation potential and Coulomb interaction between electrons; and causing the computer to decide parameters describing the model such that the obtained two fluctuations are approximately equal to each other.

According to a twentieth aspect of the invention, in order to decide a model so that the fluctuations of the physical quantities calculated as a reference system can be reproduced, a wave function of a many-body system is obtained by using a parameter defined in the process of deciding this model.

The computer program according to the twenty first invention is characterized in that the computer program uses an optimization technique based on the extended Kohn-Sham theory formulated by an expression including a wave function functional expressed by the following equation, as the first-principle calculation.

$$G_{Wi}[\Psi] = \langle \Psi|T + V_{red}|\Psi \rangle - \min_{\Psi' \to n_\Psi} \langle \Psi'|T + V_{red}|\Psi' \rangle + F[n_\Psi] + \int d^3r v_{ext}(r) n_\Psi(r) \quad \text{[Equation 9]}$$

Wherein $\Psi$ indicates a many-particle wave function, T indicates a kinetic energy operator, $n_\Psi$ indicates one-electron density, $F[n]$ indicates a universal energy functional, $\Psi'$ indicates a many-particle wave function minimizing $\langle T+V_{red} \rangle$ with a condition that one electron density $n_\Psi$ is reproduced, $v_{ext}$ indicates an external interaction potential, and $V_{red}$ indicates an operator defined by the equation 8.

According to a twenty first aspect of the invention, a ground state energy of a Coulomb system and its one-particle density are given by an optimization problem of a wave function functional expressed by equation 9.

A recording medium according to the twenty second invention is characterized in that a computer-readable recording medium recording a computer program causing a computer to calculate an electronic state of a substance by a first-principle calculation, the computer program comprising the steps of regarding physical quantities characterizing physical properties of the substance, causing the computer to decide a model to reproduce fluctuations of the physical quantities and causing the computer to calculate an electronic state of the substance by the first-principle calculation with the decided model set as an initial condition.

According to a twenty second aspect of the invention, a model for reproducing fluctuations in physical quantities characterizing properties of a substance is decided, and an electronic state is obtained by a first-principle calculation with the decided model set as an initial condition. Accordingly, when a model capable of simultaneously reproducing the fluctuations in the physical quantities, the model being capable of giving energy and one-electron density equivalent to a Schrödinger equation of an electron system showing a ground state without degeneracy, can be given as a functional regarding a wave function by using a universal energy functional, then a parameter inherent in the model is uniquely defined.

The recording medium according to the twenty third invention is characterized in that an optimization technique is used, which is based on an extended Kohn-Sham theory formulated by an expression including a residual exchange correlation energy functional expressed by the following equation, as the first-principle calculation.

$$E_{rxc}[n_\psi] = E_{xc}[n_\phi] + \min_{\Phi \to n_\Psi} \langle\Phi|T|\Phi\rangle - \min_{\Psi' \to n_\Psi} \langle\Psi'|T + V_{red}|\Psi'\rangle \quad \text{[Equation 10]}$$

Wherein $n_\Psi$ indicates one-electron density, $E_{xc}[n_\Psi]$ indicates an exchange correlation energy functional, $\Phi$ indicates a many-particle wave function in a state in which no correlation is generated, $\Psi'$ indicates the many-particle wave function in a state in which the correlation is generated, T indicates a kinetic energy operator, and $V_{red}$ indicates an operator defined by the following correlation function given by a set of physical quantities $\{X_i\}$.

$$\langle\Psi|V_{red}|\Psi\rangle = \sum_i W_i \langle\Psi|(X_i - \overline{X}_i)\cdot(X_i - \overline{X}_i)|\Psi\rangle \quad \text{[Equation 11]}$$

Wherein i=1, 2, 3, ..., N (N is the number of the physical quantities to be calculated), $W_i$ indicates a parameter expressing a weight, and a symbol in a small parenthesis indicates a difference between the physical quantities $X_i$ and a mean value of the physical quantities $X_i$.

According to a twenty third aspect of the invention, in an extended Kohn-Sham equation, residual exchange correlation energy is expressed as a normal exchange correlation energy and a difference therefrom, by an identity transformation from an exact expression. This differential part is given as the difference of a kinetic energy and an expected value of $V_{red}$, between two states of a state in which there are fluctuations to reproduce the same electron density and a state in which there are no fluctuations. Then variation in this kinetic energy is given in the frame of an extended Kohn-Sham theory, whereby calculation of the electronic state is possible without using a highly accurate calculation method such as a Quantum Monte Carlo Method and a Configuration Interaction Method.

The recording medium according to the twenty fourth invention is characterized in that an optimization technique based on an extended Kohn-Sham theory formulated by an expression including a wave function functional expressed by the following equation is used as the first-principle calculation.

$$G_{W_i}[\Psi] = \langle\Psi|T + V_{red}|\Psi\rangle - \quad \text{[Equation 12]}$$
$$\min_{\Psi' \to n_\Psi} \langle\Psi'|T + V_{red}|\Psi'\rangle + F[n_\Psi] + \int d^3 r v_{ext}(r) n_\Psi(r)$$

Wherein $\Psi$ indicates a many-particle wave function, T indicates a kinetic energy operator, $n_\Psi$ indicates one-electron density, F[n] indicates a universal energy functional, $\Psi'$ indicates the many-particle wave function minimizing $<T+V_{red}>$ with a condition that one electron density $n_\Psi$ is reproduced, $v_{ext}$ indicates an external interaction potential, and $V_{red}$ indicates an operator defined by the following correlation function given by a set of physical quantities $\{X_i\}$.

According to a twenty fourth aspect of the invention, a ground state energy of a Coulomb system and its one-particle density are given by an optimization problem of a wave function functional expressed by above-mentioned equation.

According to the present invention, the model to reproduce the fluctuations of the physical quantities characterizing the properties of the substance is decided, and the electronic state is obtained by the first-principle calculation with the decided model set as the initial condition. Accordingly, it is possible to uniquely define a parameter to describe the model capable of giving the energy and one-electron density equivalent to the Schrödinger Equation of the electron system showing the ground state without degeneracy. Therefore, the electronic state of the substance can be calculated.

According to the present invention, in the extended Kohn-Sham equation, the residual exchange correlation energy is expressed as a normal exchange correlation energy and a difference therefrom, by an identity transformation from an exact expression. This differential part is given as the difference of a kinetic energy and an expected value (fluctuations) of $V_{red}$, between two states of the state in which there are fluctuations to reproduce the same electron density and a state in which there are no fluctuations. Then variation of this kinetic energy is given in the frame of the extended Kohn-Sham theory, whereby calculation of the electronic state is possible without using the highly accurate calculation method such as the Quantum Monte Carlo Method and the Configuration Interaction Method. As a result, a high-speed calculation technique surpassing the local density approximation method can be obtained while ensuring the accuracy compatible with that of the Quantum Monte Carlo Method and the Configuration Interaction Method.

According to the present invention, by evaluating the kinetic energy and the total energy in two states of the state in which there are fluctuations to reproduce the same electron density and the state in which there are no fluctuations, the electronic state in the frame of the extended Kohn-Sham theory can be calculated.

According to the present invention, the model is decided so as to reproduce the fluctuations of the physical quantities calculated as the reference system. Accordingly, a wave function of the many-body system can be obtained by using the parameter defined in the process of deciding this model.

According to the present invention, by an optimization problem of the wave function functional expressed by the aforementioned equation, the ground state energy of the Coulomb system and its one-particle density can be given.

According to the present invention, the definition of the effective potential is possible, which is given by applying density variation to the Legendre transformation of the energy functional including the exchange energy and the correlation energy. Therefore, it is possible to use the expression that the interacted virtual electron system is moved in the effective integral Hamiltonian composed of the kinetic energy portion of Hamiltonian and this effective potential. Accordingly, the expression of a certain localized orbital can be obtained as a solution of the effective Hamiltonian, from a Wannier function immediately obtained by inverse Fourier transformation generalized from a set of proper band indices after obtaining a Bloch wave when, for example, crystallization is taken into consideration.

According to the present invention, by using the Quantum Monte Carlo Method, the Transcorrelated Method, the Configuration Interaction Method, the Perturbational Calculation/Green's function method, or the effective potential method, the fluctuations of the physical quantities in the many-body electron system can be obtained as the reference system.

According to the present invention, the fluctuations of the physical quantities can be obtained based on the extended Kohn-Sham theory, using the plane wave basis expansion method, the reinforced plane wave basis expansion method, the actual space, the numerical value basis expansion method, the mixed basis expansion method, the localized basis expansion method, or the linear MT orbital method.

According to the present invention, the fluctuations of the physical quantities are described by the two-dimensional correlation function having the positive definite and the bounded value range. Therefore, when the model capable of simultaneously reproducing the correlation function of the positive definite and the bounded value range, the model being capable of giving energy and one-electron density equivalent to those of a Schrödinger Equation of an electron system showing the ground state without degeneracy, can be given by using the universal energy functional, then a parameter inherent in the model is uniquely defined.

According to the present invention, the physical quantities are described as numerical operators or generation/annihilation operators regarding the electrons in the localized orbital, and therefore the corresponding extended Kohn-Sham model is obtained as a strong correlation electron model including a first principle impurity Anderson Model and a first principle Hubbard model.

According to the present invention, by deciding the model to reproduce the fluctuations of the physical quantities, the structural factor of the substance (namely the atomic arrangement in the atomic level) is defined. Therefore, all other physical quantities can be defined with no contradiction and without a prerequisite.

The above and further objects and features will more fully be apparent from the following detailed description with accompanying drawings.

DETAILED DESCRIPTION

Specific description will be given hereinafter with reference to the drawings.

Embodiment 1

Figure 1:
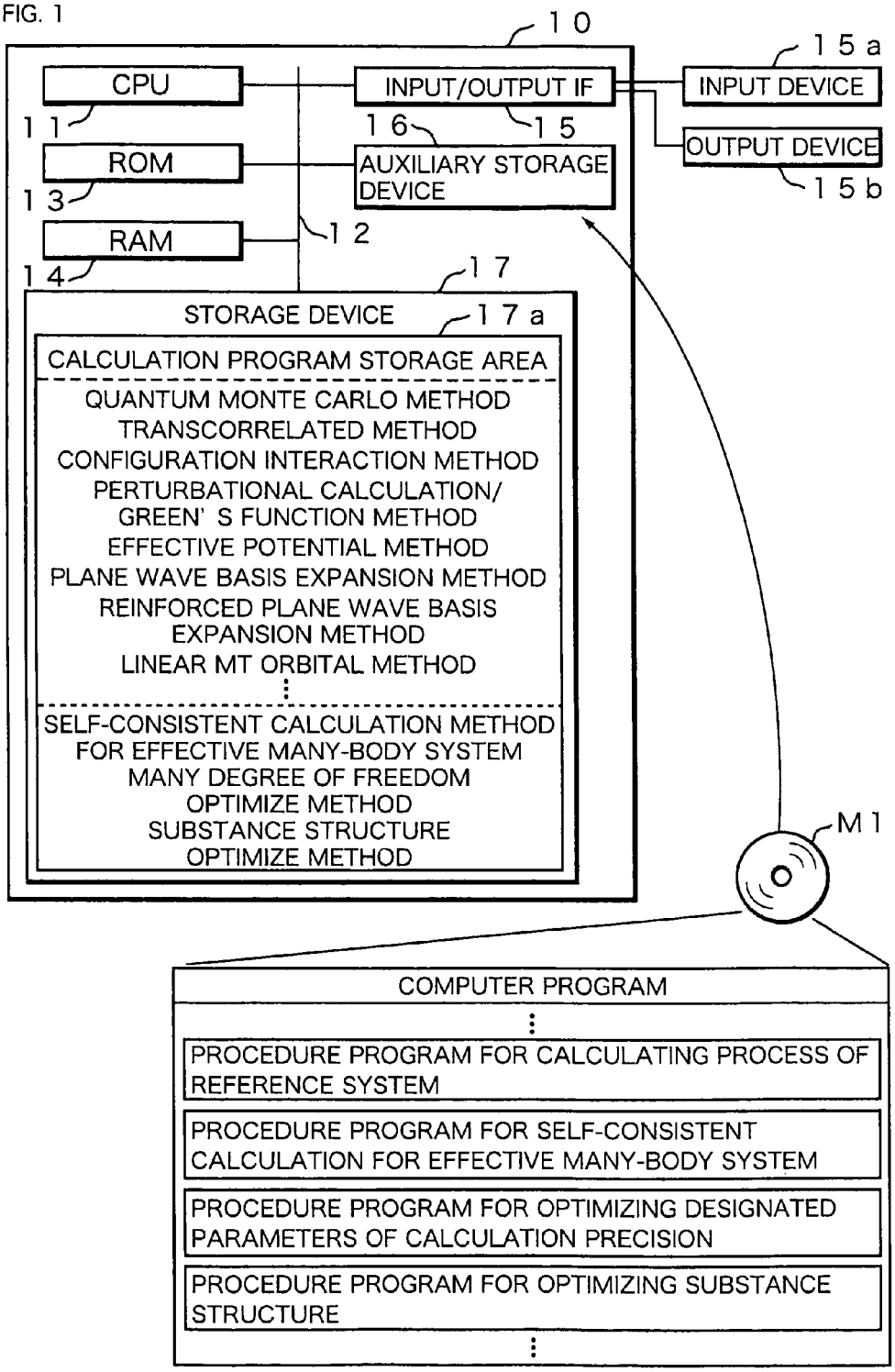
FIG. 1 is a block diagram illustrating an internal structure of an electronic state calculation device according to Embodiment 1.

FIG. 1 is a block diagram illustrating an internal structure of an electronic state calculation device according to Embodiment 1. The electronic state calculation device 10 includes a CPU 11, a ROM 13, a RAM 14, an input/output IF 15, an auxiliary storage device 16, and a storage device 17, and each hardware of them is connected to one another via a bus 12. A control program for controlling each part of the hardware is stored in the ROM 13. The CPU 11 controls the aforementioned each part of the hardware, by loading and executing the control program stored in the ROM 13 on the RAM 14. An input device 15a such as a mouse and a keyboard, CRT, and an output device 15b such as a liquid crystal display are connected to the input/output IF 15. The input/output IF 15 performs control regarding input/output of information inputted through the input/output device 15a and information to be outputted to the output device 15b.

The auxiliary storage device 16 includes a reading device such as an FD drive and a CD-ROM drive for reading the aforementioned computer program from a storage medium M1 such as an FD and a CD-ROM recording the computer program for causing the computer to execute an electronic state calculation method described in this embodiment. The computer program read by the auxiliary storage device 16 is stored in the storage device 17. The CPU 11 realizes the electronic state calculation method as described below, by loading and executing the computer program stored in the storage device 17 on the RAM 14.

Note that as the storage medium M1 recording the computer program, other than the aforementioned FD and the CD-ROM, it is also possible to utilize an optical disc such as an MO, an MD, or a DVD-ROM, a magnetic recording medium such as a hard disk, a card type recording medium such as an IC card, a memory card, and an optical card, a semiconductor memory such as a mask ROM, an EPROM (Erasable Programmable Read Only Memory), an EEPROM (Electrically Erasable Programmable Read Only Memory), or a flash ROM. In addition, by constituting a system in which a communication network including the Internet can be connected, the aforementioned computer program may be downloaded from the communication network. Further, the aforementioned computer program may also be stored in the ROM 13 in advance.

The storage device 17 is, for example, a hard disk drive, in which initial data necessary for calculating an electronic state and data obtained by calculation of the electronic state are stored. Also, a part of this storage capacity is utilized as a calculation program storage area 17a in which a calculation program based on various calculation techniques is stored. A calculation program based on a Quantum Monte Carlo Method, a Transcorrelated Method, a Configuration Interaction Method, a Perturbational Calculation/Green's function method, or an effective potential method, a plane wave basis expansion method, a reinforced plane wave basis expansion method, a linear MT orbital method, can be given as the calculation program stored in this calculation program storage area 17a. Note that the calculation technique used in the calculation of the electronic state is not necessarily limited to the above-described calculation methods, and various accurate calculation techniques to be obtained in an electronic state calculation field can be used in the future.

Figure 2:
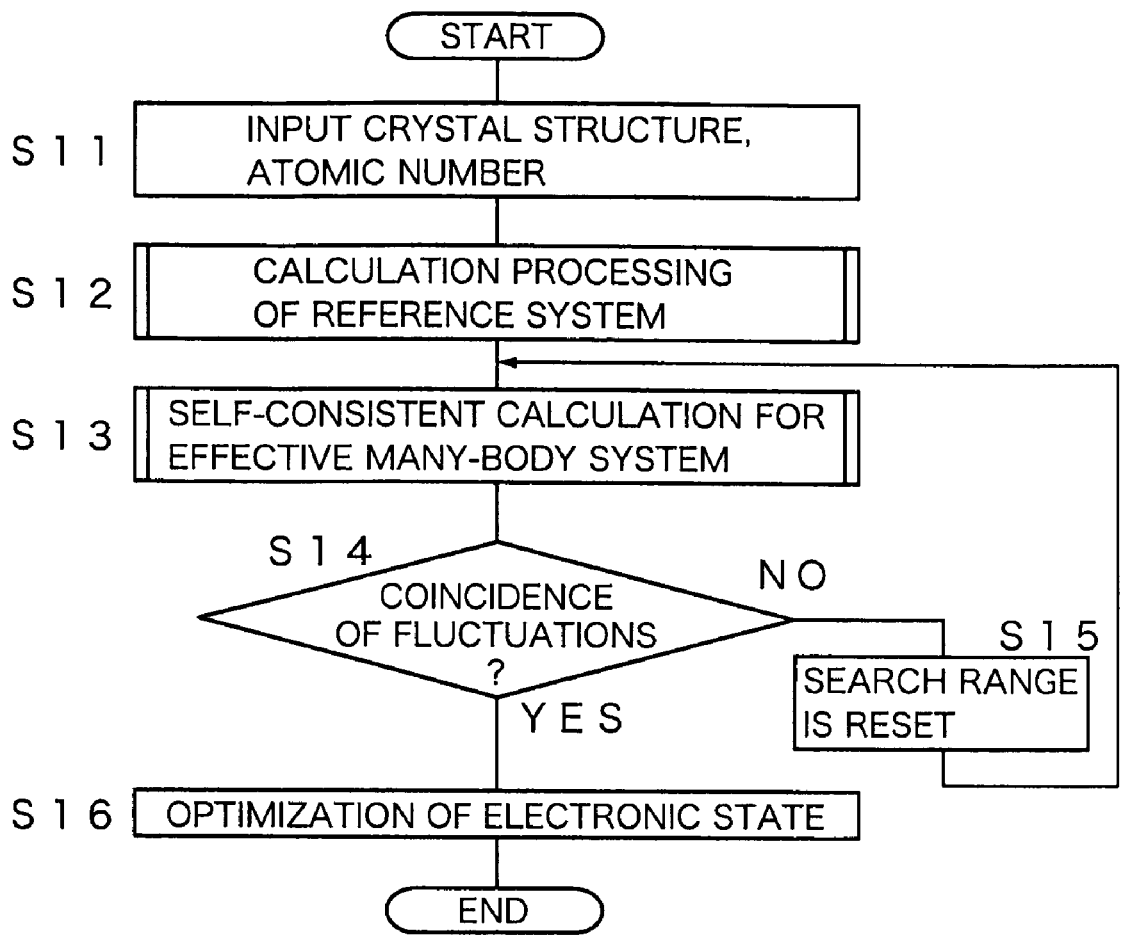
FIG. 2 is a flowchart showing a procedure of processing executed by the electronic state calculation device.

The electronic state calculation method according to this embodiment will be described below. Note that in this embodiment, an optimizing calculation of the electronic state for a known crystal structure will be described. FIG. 2 is a flowchart showing a procedure of processing executed by the electronic state calculation device 10. First, the electronic state calculation device 10 receives the crystal structure of a crystal to be a calculation object, and an input of the atomic number of an atom constituting this crystal structure, through the input device 15a (step S11). Subsequently, the electronic state calculation device 10 performs calculation processing of a reference system (step S12). In this calculation processing of the reference system, the atom that can generate fluctuations and atomic groups around this atom are specified by the electric state calculation based on a normal Kohn-Sham theory.

Figure 3:
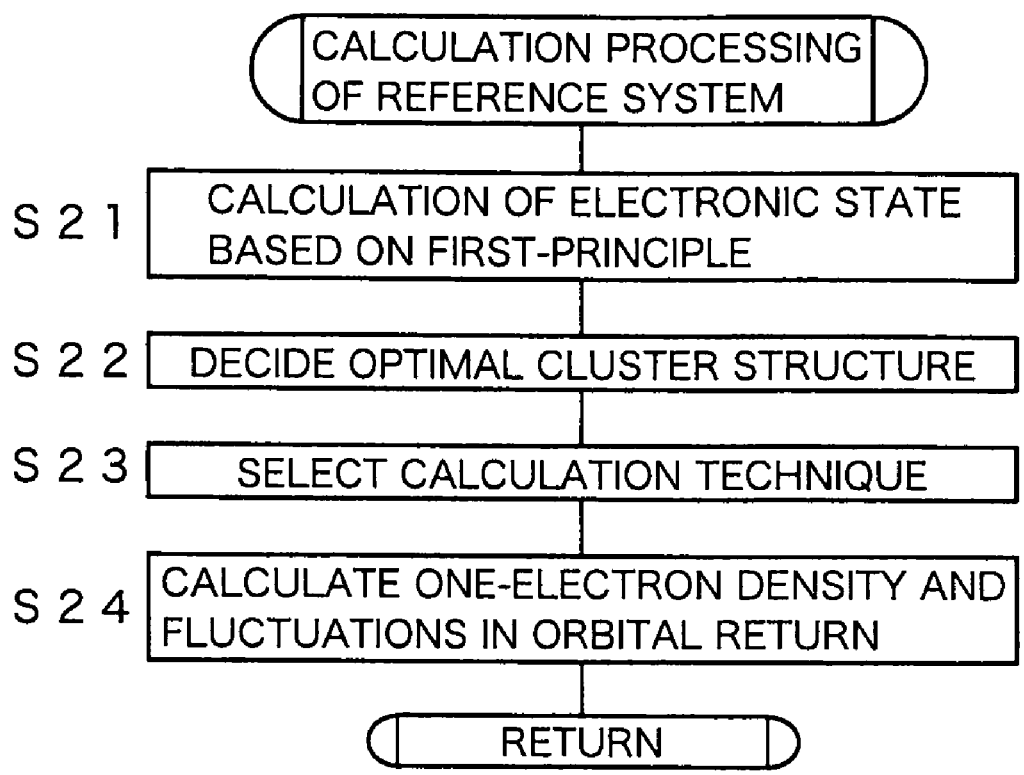
FIG. 3 is a flowchart showing calculation processing of a reference system.

FIG. 3 is a flowchart showing the calculation processing of the reference system. The electronic state calculation device 10 performs calculation of the electronic state based on a first-principle (step S21), and decides an optimal cluster structure (step S22). That is, the atom that can generate fluctuations and the atomic groups around this atom are specified from the electronic state calculation by the normal Kohn-Sham equation.

Subsequently, the electronic state calculation device 10 selects a calculation technique by selecting a calculation program stored in the calculation program storage area 17a (step S23), and calculates one-electron density and the fluctuations in an orbital by using the selected calculation technique (step S24). A quantum state given by the Kohn-Sham equation is expressed by a single slater product, which is a solution of an independent fermion system without interaction. However, it is so regarded that one-particle spectrum structure given by the Kohn-Sham equation has originally no meaning, and it is known that one of the exact expressions is given by formulating it as an optimization problem of an energy functional regarding a wave function of a virtual independent fermion system. An formulation as described below is employed herein.

$$G_0[\Psi] = \langle\Psi|T|\Psi\rangle - \min_{\Psi'\to n_\Psi}\langle\Psi'|T|\Psi'\rangle + F[n_\Psi] + \quad \text{(Equation 13)}$$

$$\int d^3 r v_{ext}(r) n_\Psi(r)$$

$$= \langle\Psi|T|\Psi\rangle + \frac{1}{2}\int \frac{n_\Psi(r)n_\Psi(r')}{|r-r'|} d^3 r d^3 r' +$$

$$E_{xc}[n_\Psi] + \int d^3 r v_{ext}(r) n_\Psi(r)$$

Here, a so-called exchange correlation energy functional is defined as follows from the above-described equation.

$$E_{xc}[n_\Psi] = \min_{\Psi'\to n_\Psi}\langle\Psi'|T+V_{ee}|\Psi'\rangle - \quad \text{(Equation 14)}$$

$$\min_{\Psi'\to n_\Psi}\langle\Psi'|T|\Psi'\rangle - \frac{1}{2}\int \frac{n_\Psi(r)n_\Psi(r')}{|r-r'|} d^3 r d^3 r'$$

A methodology of the electronic state calculation using $G_0[\Psi]$ has already been widely known, and various physical quantities can be immediately calculated. As the reference system, when the fluctuations can be measured by an experiment using an actual substance, a result thereof can be used. When the experiment is not possible, the fluctuations are evaluated by using a high accuracy calculation capable of directly solving the Schrödinger Equation. A technique selected in step S23 is used in the high accuracy calculation. At this time, the Quantum Monte Carlo Method, the Transcor-related Method, the Configuration Interaction Method, the Perturbational Calculation/Green's function are used. Also, in an actual calculation, the data of the optimal cluster structure decided in step S22, a parameter inherent in a model obtained by a self-consistent calculation of a many-body system as will be described later, and the data of a localized orbital are used.

The Kohn-Sham theory is introduced based on a density functional theory. One-particle density is defined therein, and other physical quantities must be individually formulated. Note that when numerical operators in a localized orbital $\Phi_i(r)$ is used as a physical quantity $X_i$, the corresponding extended Kohn-Sham model is obtained as a strong correlation electron model including a first-principle impurity Anderson Model and a first-principle Hubbard model.

Description is returned to the flowchart of FIG. 2. The electronic state calculation device 10 performs the self-consistent calculation for an effective many-body system after calculation processing of the reference system (step S13). In this self-consistent calculation, the fluctuations or the correlation function is obtained based on the extended Kohn-Sham theory proposed by the present inventors, and an effective many-body wave function is decided. Note that the details of the calculation technique will be described later.

Subsequently, the electronic state calculation device 10 compares the fluctuations calculated for the reference system and the fluctuations calculated for the effective many-body system by using the self-consistent calculation, and decides whether or not both of them coincides with each other (step S14). When it is so determined that both of them do not coincide with each other (NO: S14), a search range of the parameter to describe an effective model is reset (step S15), and the processing is returned to step S13.

When it is so determined that both of them coincide with each other (YES: S14), namely, when the effective many-body wave function is obtained by utilizing the effective model decided to reproduce the fluctuations, as the initial condition in the first-principle calculation, optimization of the electronic state for the known crystal structure is performed (step S16).

Figure 4:
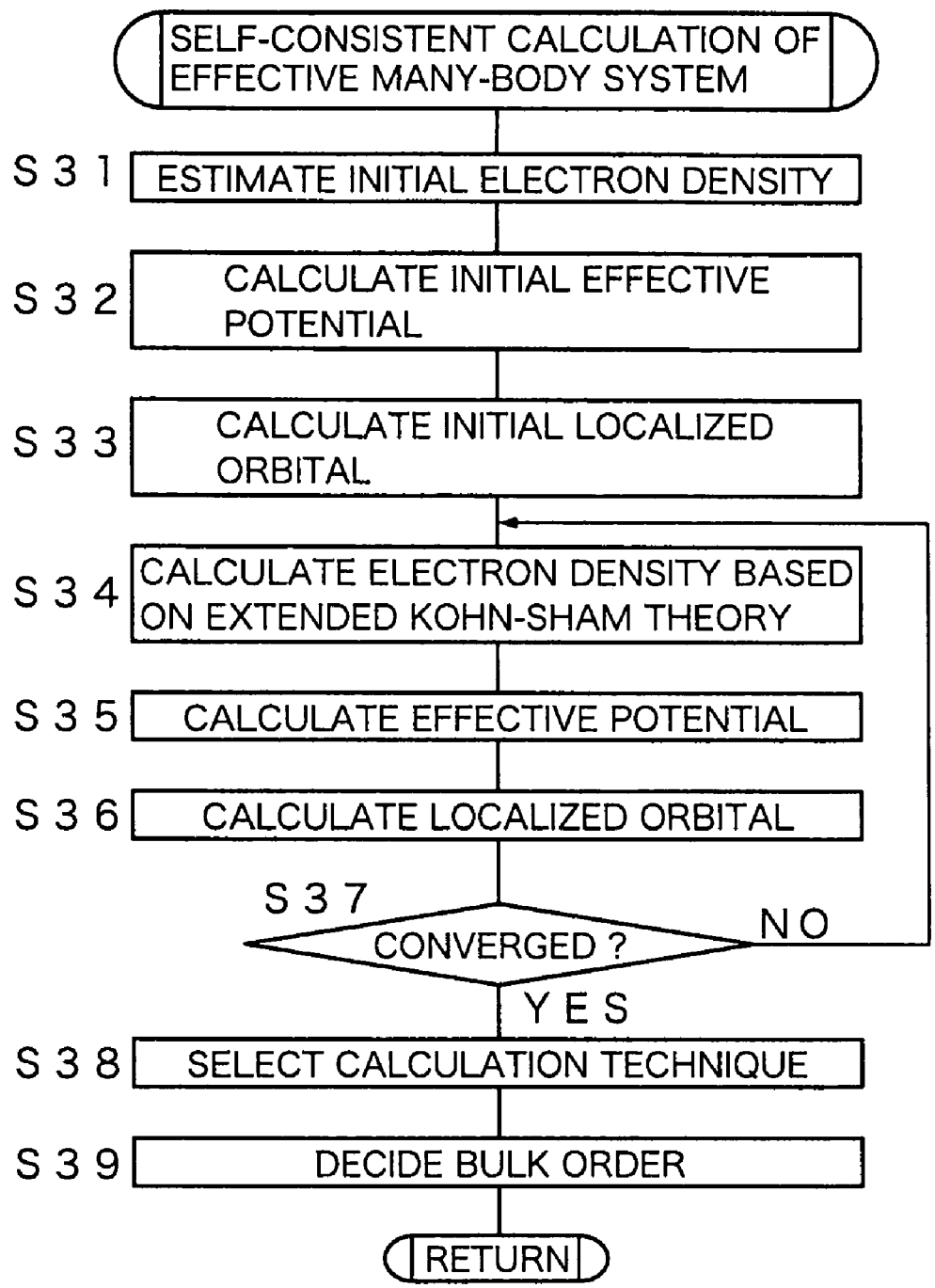
FIG. 4 is a flowchart illustrating the procedure of the processing executed by the electronic state calculation device in a self-consistent calculation of an effective many-body system.

FIG. 4 is a flowchart illustrating the procedure of the processing executed by the electronic state calculation device 10 in the self-consistent calculation of the many-body system. The electronic state calculation device 10 estimates an initial electron density based on the normal Kohn-Sham theory (step S31), and calculates an initial effective potential and an initial localized orbital (steps S32, S33).

When based on prescription of a density functional method, it is possible to define the effective potential which is given as a density variation of the energy functional including the exchange energy and the correlation energy. That is, it is possible to use the expression that a virtual electron system is moved in the effective integral Hamiltonian composed of a kinetic energy portion and an effective potential of the Hamiltonian. In this case, the expression of a certain localized orbital can be obtained as a solution of the effective integral Hamiltonian, from a Wannier function immediately obtained by inverse Fourier transformation generalized from a set of proper band indices after obtaining a Bloch wave, when, for example, crystallization is taken into consideration. Generally, as such a localized orbital, there generate a group of orbitals in which the number of occupancy is allowed to fluctuate in a quantized energy structure that appears in the effective integral Hamiltonian. In this embodiment, a numerical operator $n_i$ for evaluating the fluctuations is defined accompanying a group $\phi_i$ of a normalized and orthogonalized localized orbital for expressing a level in the vicinity of a fermionic order. Accordingly, the following quantity is defined as density/density correlation function on $\phi_i(r)$.

$$\langle n_i^2 \rangle \equiv \langle (n_{i,\uparrow} + n_{i,\downarrow} - \bar{n}_{i,\uparrow} - \bar{n}_{i,\downarrow})^2 \rangle \qquad \text{(Equation 15)}$$

Here, generation/annihilation operators are given accompanying the normalized orbital $\phi_i(r)$. Numerical operator $n_{i,\sigma}$ measures the number of electrons in this orbital. By giving a quantum state $|\Psi\rangle$, an expected value of $n_i$ is given as $\langle\Psi|n_{i,\sigma}|\Psi\rangle$.

Subsequently, the electronic state calculation device 10 calculates the electron density, the effective potential, and the localized orbital based on the extended Kohn-Sham theory (steps S34 to S36). In the first-principle calculation, a functional such as $G_{wi}[\Psi]$ based on the extended Kohn-Sham theory and a residual exchange correlation energy functional $E_{rxc}[n]$ are used in this embodiment, to improve the accuracy of the functional such as $G_0[W]$ giving the electronic state calculation based on the Kohn-Sham theory based on a density functional method. At this time, suitable fluctuations of the physical quantity $X_i$ are expressed as follows.

$$\langle\Psi|(X_i-\overline{X}_i)\cdot(X_i-\overline{X}_i)|\Psi\rangle \qquad \text{(Equation 16)}$$

Regarding this equation, a method of defining a parameter $W_i$ of the model is used to reproduce a value of a properly defined reference system. In a case of the normal Kohn-Sham theory, the fluctuations cannot be reproduced in a model given by $G_0[\Psi]$. However, in the extended Kohn-Sham theory, the fluctuations can be reproduced, and therefore the accuracy of the corresponding model is remarkably improved in the point of reproduction of various physical properties. Here, the fluctuations of the physical quantities is described by a two-dimensional correlation function having a positive definite and a bounded value range. By increasing the number and the kind of the physical quantities introduced as the fluctuations, reproduction of which is requested, the accuracy of the model can be improved. The functional $G_{wi}[\Psi]$ based on the extended Kohn-Sham theory is given by the equation described below.

$$G_{Wi}[\Psi] = \langle\Psi|T + V_{red}|\Psi\rangle - \min_{\Psi' \to n_\Psi}\langle\Psi'|T + V_{red}|\Psi'\rangle + \qquad \text{(Equation 17)}$$
$$F[n_\Psi] + \int d^3 r v_{ext}(r) n_\Psi(r)$$
$$= \langle\Psi|T + V_{red}|\Psi\rangle +$$
$$\frac{1}{2}\int \frac{n_\Psi(r)n_\Psi(r')}{|r-r'|} d^3 r d^3 r' +$$
$$E_{rxc}[n_\Psi] + \int d^3 r v_{ext}(r) n_\Psi(r)$$

Here, by using the correlation function given by the set of the physical quantities $\{X_i\}$ defined by the following equation, $V_{red}$ is defined as follows.

$$\langle\Psi|V_{red}|\Psi\rangle = \sum_i W_i \langle\Psi|(X_i - \overline{X}_i)\cdot(X_i - \overline{X}_i)|\Psi\rangle \qquad \text{(Equation 18)}$$

The corresponding residual exchange correlation function is given as follows.

$$E_{rxc}[n_\Psi] \min_{\Psi' \to n_\Psi}\langle\Psi'|T + V_{ee}|\Psi'\rangle - \qquad \text{(Equation 19)}$$
$$\min_{\Psi \to n_\Psi}\langle\Psi'|T + V_{red}|\Psi'\rangle - \frac{1}{2}\int\frac{n_\Psi(r)n_\Psi(r')}{|r-r'|}d^3 r d^3 r'$$

When the calculation is conducted, approximation should be introduced to residual exchange correlation energy functional $E_{rxc}[n]$. The final result depends on accuracy of the approximation, and therefore improvement of the accuracy of an evaluation of the residual exchange correlation energy functional $E_{rxc}[n]$ leads to improvement of the calculation accuracy.

An evaluation method of the residual exchange correlation energy functional $E_{rxc}[n]$ will be described below. An exact value is given by the equation 19 to the residual exchange correlation energy functional $E_{rxc}[n]$. In an optimization process such as min ($\Psi' \to n_{\Psi'}$), search defined in a phase space of the wave function is performed. Although this is a restriction-attached search, this search can be executed by Lagrange's method of undetermined coefficient whereby an undetermined coefficient is set at each point in the space. Alternately, Legendre transformation is performed and this is redefined as an optimization problem of potential, and thereafter this problem may be solved.

Next, the electronic state calculation device 10 performs convergence determination, and determines whether or not the calculation is converged (step S37). The wave function of the Configuration Interaction expressed by a linear combination of the slater product can be given as the solution of $G_{wi}[\Psi]$ corresponding to a multi-reference density functional method. At this time, an integral Hamiltonian portion of the effective model is decided again through one-particle density obtained from $\Psi$, and therefore an integral portion is changed in the middle of the calculation. However, in a stage in which the structure of the given phase space becomes invariable, the phase space is set by giving an algorithm giving a partial space where effective interaction is generated as a unitary transformation to define the partial space from the whole phase space. In this case, it is only the set of $W_i$ that determines the weight between configurations as a result of effective interaction. Accordingly, it is possible to find one-to-one correspondence between the set of $W_i$ and the structure of $\Psi$, in the convergence stage of the calculation.

When it is so determined that the calculation is not converged in step S37 (NO: S37), the electronic state calculation device 10 returns the processing to step S34. Also, when it is so determined that the calculation is converged in step S37 (YES: S37), an effective model having a decided configuration as a minimum energy state is defined by obtaining the set of $W_i$. This embodiment adopts a method of reversely deciding the Hamiltonian having its self-consistent solution as an intrinsic solution, after obtaining the aforementioned solution in advance. The reason why this method can be executed by this multi-reference density functional method is based on a theory proposed by the present inventors such that any fluctuation and a model having effective interaction generated in association with these fluctuations are established at least as a density functional theory.

Thus, the fluctuations corresponding to the set of $W_i$ is finally decided. It is possible to employ a plurality of extended Kohn-Sham systems in which the physical quantities are specified, as proper extended Kohn-Sham models. The change of the fluctuations in the case of changing the set of $W_i$ is thus defined, and therefore the model that fits the final reference system can be obtained.

In addition, in the process of deciding the self-consistent solution, the set of the orbitals for setting the effective interaction and a form of the interaction are all decided by the kind and the number of fluctuations that are taken into consideration. An indicator for performing verification of whether or not a sufficient effective model can be obtained, is the point that physical properties (energy, one-electron density, various order variables, fluctuations, and the like) of the model are not changed, which are shown by the model given when the kind and the number of the fluctuations that are taken into consideration are changed.

Subsequently, the electronic state calculation device 10 performs selection of the calculation technique by selecting the calculation program stored in the calculation program storage area 17a (step S38), and by deciding a coefficient matrix of the effective many-body wave function using the selected calculation technique, a bulk order is decided (step S39). As the calculation technique selected here, an exact diagonalization method, the Quantum Monte Carlo method, a numerical renormalization group method, a dynamic mean field approximation method, and the like can be given.

Embodiment 2

In Embodiment 1, description is given for the optimizing calculation of the electronic state in the known crystal structure. However, dynamics of a system may be calculated by using the technique of Molecular Dynamics. Note that the internal structure of the electronic state calculation device 10 is completely the same as that of Embodiment 1, and therefore description therefore is not given.

Figure 5:
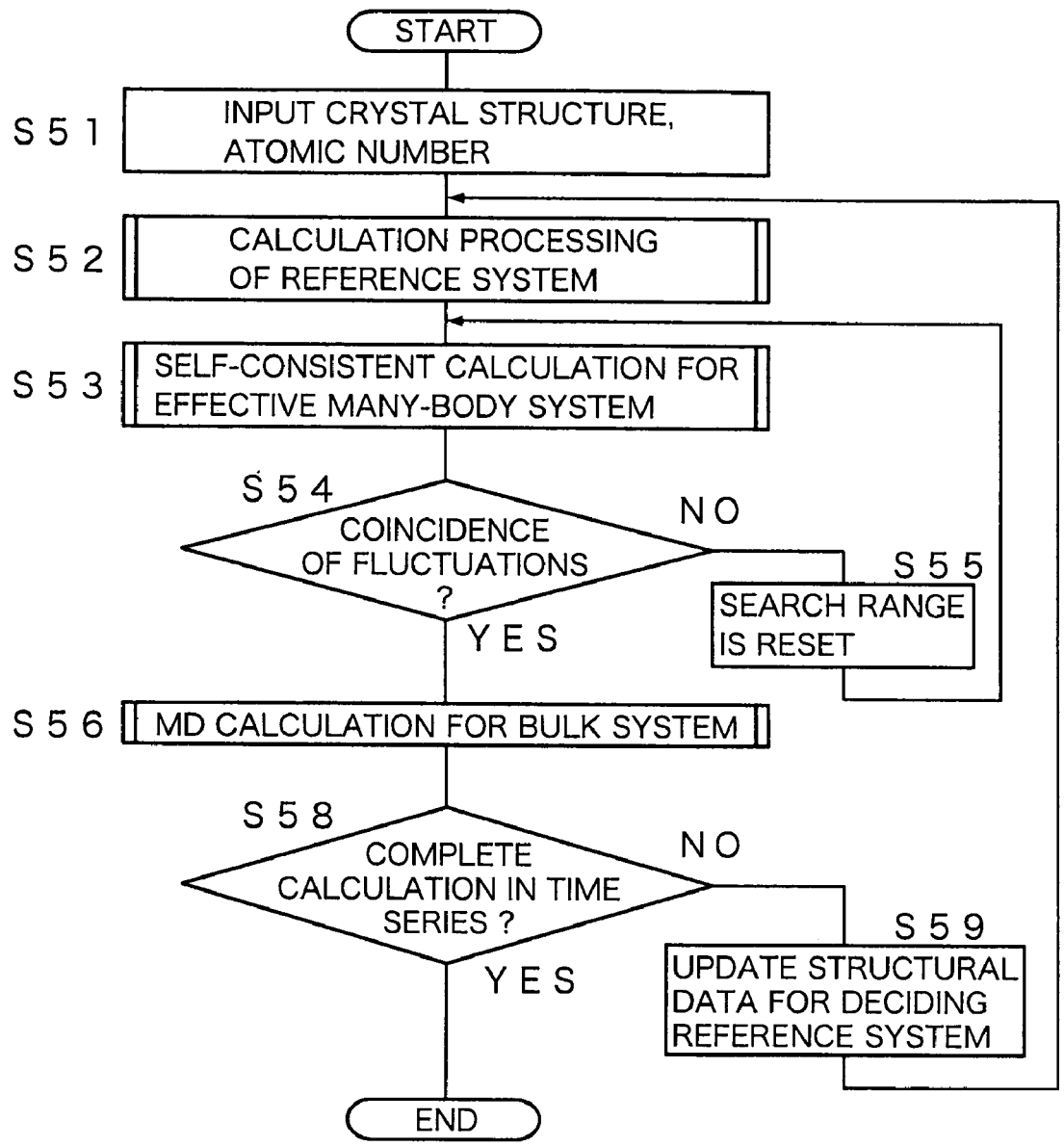
FIG. 5 is a flowchart showing the procedure of the processing executed by the electronic state calculation device.

FIG. 5 is a flowchart showing the procedure of the processing executed by the electronic state calculation device 10. First, the electronic state calculation device 10 receives a crystal structure of the crystal to be a calculation object, and the input of the atom number of the atom constituting this crystal structure, through the input device 15a (step S51). Subsequently, the electronic state calculation device 10 performs calculation processing of the reference system (step S52). This calculation processing of the reference system is completely the same as the processing content described by the flowchart of FIG. 3, and the atom that can generate the fluctuations and the atom group around this atom are specified by the electronic state calculation based on the normal Kohn-Sham theory.

Next, the electronic state calculation device 10 performs the self-consistent calculation for the effective many-body system (step S53). This self-consistent calculation is completely the same as the processing contents described by the flowchart of FIG. 4, and therefore the density/density correlation function is obtained based on the extended Kohn-Sham theory proposed by the present inventors, and the effective many-body wave function is decided.

Next, the electronic state calculation device 10 compares the fluctuations calculated for the reference system, and the fluctuations calculated for the effective many-body system using the self-consistent calculation, and determines whether or not both of them coincide with each other (step S54). When it is so determined that both of them do not coincide with each other (NO: S54), a search range of the parameter describing the effective model is reset (step S55), and the processing is returned to step S53.

When it is determined that both of them coincide with each other (YES: S54), namely, by utilizing the effective model decided so as to reproduce the fluctuations as the initial condition in the first-principle calculation, the effective many-body wave function in a certain time development step is obtained. In this case, MD calculation (MD: Molecular Dynamics) is performed for a bulk system (step S56). Note that the calculation technique will be described in detail later.

Next, the electronic state calculation device 10 determines whether or not the calculation in time series is completed, based on a result of the MD calculation (step S58). When it is so determined that the calculation is not completed (NO: S58), the electronic state calculation device 10 returns the processing to step S52, after updating structural data for deciding the reference system (step S59). When it is so determined that the calculation in time series is completed (YES: S58), the processing according to this flowchart is ended.

Figure 6:
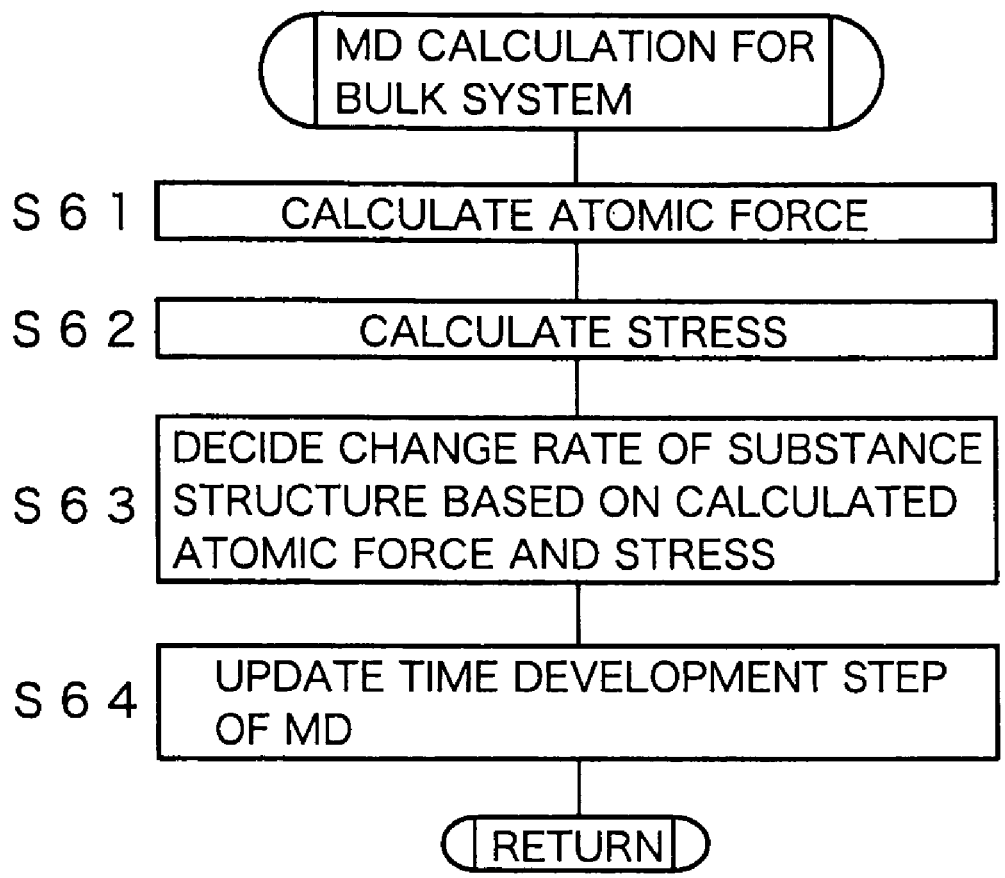
FIG. 6 is a flowchart illustrating the procedure of the processing executed by the electronic state calculation device in MD calculation applied to a bulk system.

FIG. 6 is a flowchart illustrating the procedure of the processing executed by the electronic state calculation device 10 in the MD calculation performed to the bulk system. The electronic state calculation device 10 calculates an atomic force and a stress by using the electron density the effective potential, and the localized orbital, obtained based on the extended Kohn-Sham theory (steps S61 and S62).

Next, the electronic state calculation device 10 decides a change rate of a substance structure based on the calculated atomic force and stress (step S63). Then, the electronic state calculation device 10 decides the substance structure after elapse of a minute time, and updates the time development step of MD (step S64).

Embodiment 3

Embodiment 1 and Embodiment 2 provide a structure in which the fluctuations calculated for the reference system by using a highly accurate calculation technique such as the Quantum Monte Carlo Method and the Configuration Interaction Method, and the fluctuations calculated by utilizing the self-consistent calculation based on the extended Kohn-Sham theory are compared, and the parameter is decided for describing the effective model so that both fluctuations coincide with each other. However, according to such a technique, by comparing the fluctuations between the calculation by the Quantum Monte Carlo Method, the Configuration Interaction Method, and the self-consistent calculation, calculation accuracy of the electrons state is increased for the first time. Therefore, when the self-consistent calculation based on the extended Kohn-Sham theory is used alone, there is no indicator increasing the calculation accuracy. Accordingly, in this embodiment, description will be given for a technique of using solely the self-consistent calculation based on the extended Kohn-Sham theory and calculating the electronic state.

Figure 7:
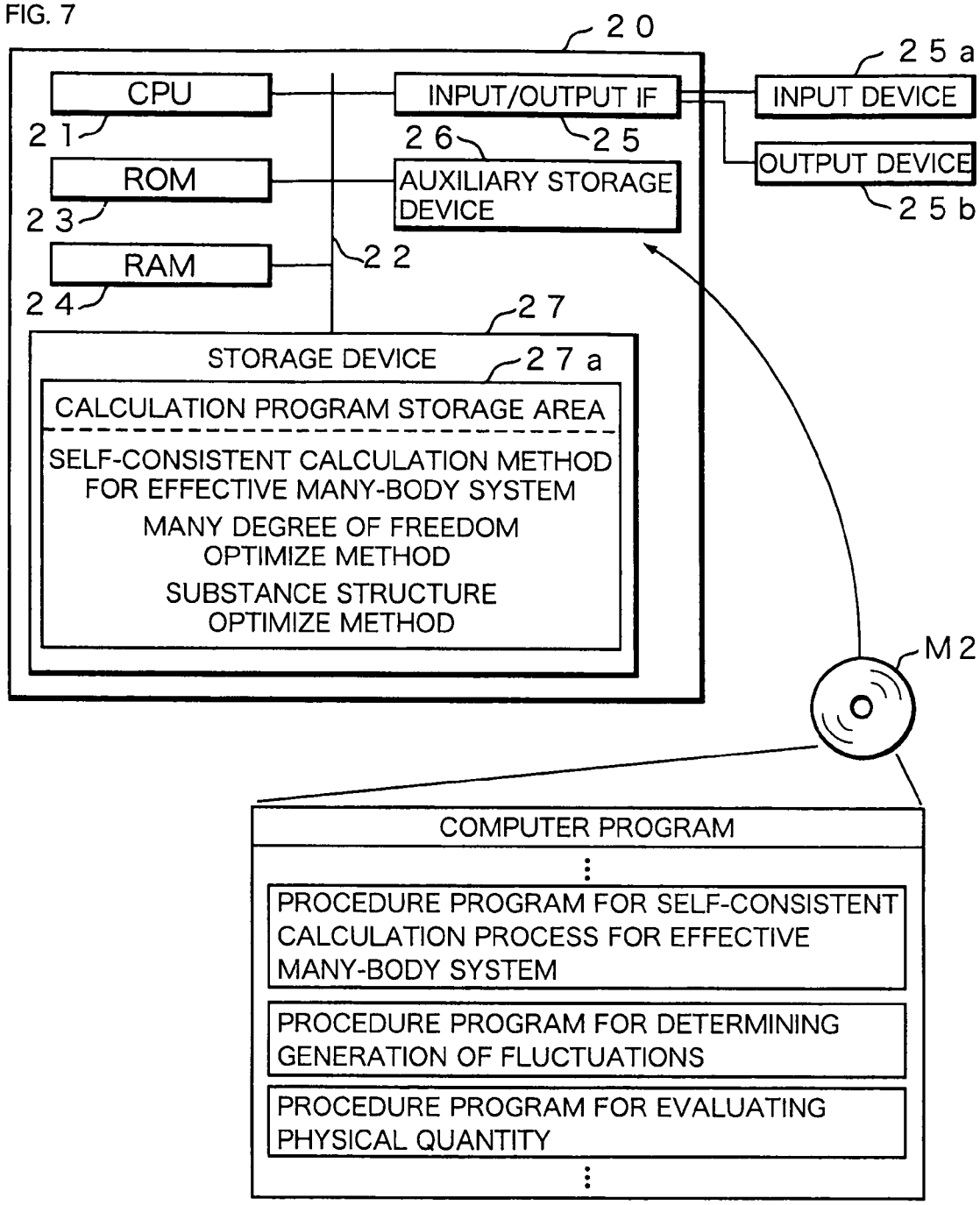
FIG. 7 is a block diagram illustrating the internal structure of the electronic state calculation device according to Embodiment 3.

FIG. 7 is a block diagram illustrating the internal structure of the electronic state calculation device according to Embodiment 3. An electronic state calculation device 20 has the same structure as that of the electronic state calculation device 10 described in Embodiment 1, and includes a CPU 21, a ROM 23, a RAM 24, an input/output IF 25, an auxiliary storage device 26, and a storage device 27, each hardware of them being connected with one another via a bus 22. In addition, an input device 25a such as a mouse and a keyboard, a CRT, and an output device 25b such as a liquid crystal display are connected to the input/output IF 25. The input/output IF 25 performs control regarding input/output of the information inputted through the input device 25a and the information outputted to the output device 25b.

The auxiliary storage device 26 includes a reading device such as an FD drive and a CD-ROM drive for reading a computer program from a recording medium M2 such as an FD and a CD-ROM in which the computer program for causing the computer to execute the electronic state calculation method to be described in this embodiment. The computer program read by the auxiliary storage device 26 is stored in the storage device 27. The CPU 21 realizes the electronic state calculation method described hereinafter, by loading and executing the computer program stored in the storage device 27 on the RAM 24.

Note that as the recording medium M2 for recording the computer program, in addition to the aforementioned FD and the CD-ROM, it is also possible to utilize an optical disc such as an MO, an MD, or a DVD-ROM, a magnetic recording medium such as a hard disk, a card type recording medium such as an IC card, a memory card, or an optical card, and a semiconductor memory such as a mask ROM, an EPROM (Erasable Programmable Read Only Memory), an EEPROM (Electrically Erasable Programmable Read Only Memory), or a flash ROM. In addition, by constituting a system in which a communication network including the Internet, the aforementioned computer program may be downloaded from the communication network. Further, the aforementioned computer program may be previously stored in the ROM 23.

The storage device 27 is, for example, a hard disk drive, in which initial data necessary for the calculation of the electronic state and the data obtained by the calculation of the electronic state are stored, with a part of this storage capacity being utilized as a calculation program storage area 27a storing a calculation program based on the self-consistent calculation method and a physical quantity evaluation method by the extended Kohn-Sham theory, and a physical quantity evaluation method by a conventional Kohn-Sham theory, and the like.

Figure 8:
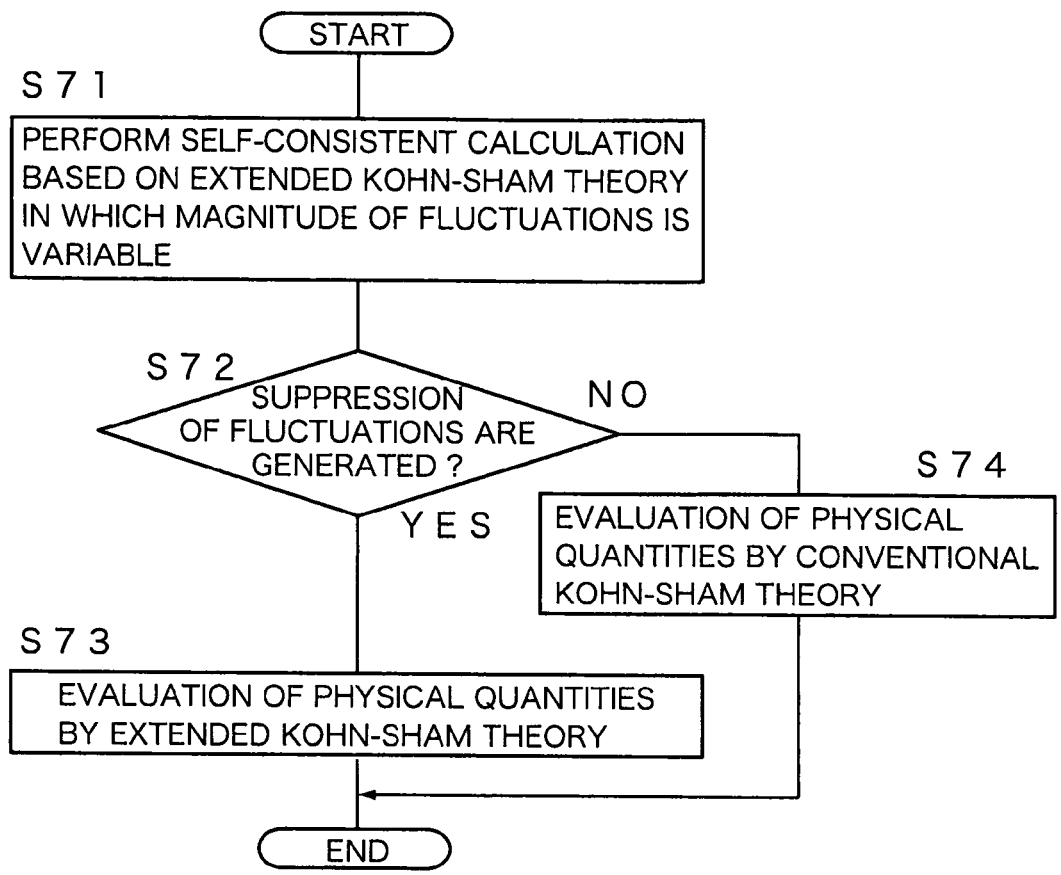
FIG. 8 is a flowchart showing the procedure of the processing executed by the electronic state calculation device.

The electronic state calculation method according this embodiment will be described below. FIG. 8 is a flowchart showing the procedure of the processing executed by the electronic state calculation device 20. The electronic state calculation device 20 performs self-consistent calculation based on the extended Kohn-Sham theory in which a magnitude of fluctuations is variable (step S71).

In the extended Kohn-Sham equation, the energy of the ground state can be described as follows.

$$E_0 = F[n_{GS}] + \int d_3 r v_{ext}(r) n_{GS}(r) \quad \text{(Equation 20)}$$

$$= \min_{\Psi} \left\{ \begin{array}{l} \langle \Psi | T + V_{red} | \Psi \rangle + \\ \int \frac{n_\Psi(r) n_\Psi(r')}{|r - r'|} d^3 r d^3 r' + \\ \int d^3 r v_{ext}(r) n_\Psi(r) + E_{rxc}[n_\Psi] \end{array} \right\}$$

Here, $n_{GS}$ indicates one-electron density in the ground state, F indicates a universal energy functional, and $v_{ext}$ indicates an external interaction potential. Also, T indicates a kinetic energy operator, $V_{red}$ indicates the fluctuations defined by the equation 18, $n_i, \sigma$ indicates a numerical operator regarding electrons, and $E_{rxc}[n_\Psi]$ indicates a residual exchange correlation energy functional.

The corresponding residual exchange correlation energy functional can be described by the following equation as a normal exchange correlation energy and a difference therefrom, by identity transformation from an exact expression shown in the equation 19.

$$E_{rxc}[n_\psi] = E_{xc}[n_\psi] + \min_{\Phi \to n_\Psi} \langle \Phi | T | \Phi \rangle - \min_{\Psi' \to n_\Psi} \langle \Psi' | T + V_{red} | \Psi' \rangle \quad \text{(Equation 21)}$$

Here, $E_{xc}[n_\Psi]$ is an exchange correlation energy functional and is a part that can be evaluated by using LDA and GGA, which are a conventional approximation theory. In addition, $\Phi$ is the wave function in a state where no correlation is generated, and $\Psi'$ is the wave function in a state where correlation is generated. That is, the second term and the third term in the right side of the equation 21 show expected values of the difference of the kinetic energy and $V_{red}$ in two states of a state in which the fluctuations exists to reproduce the same electron density and a state in which no fluctuations exist.

Thus, after deciding $\Psi$ by an effective many-electron equation, a part of the exchange correlation energy functional is evaluated by using LDA and GGA, and the difference of the kinetic energy of the equation 21 is evaluated, whereby energy E0 in the ground state can be evaluated. That is, in the evaluation of the equation 21, when the kinetic energy given by $\Psi'$ is greater than the kinetic energy given by $\Psi$, this shows that a lower state of the energy is generated by the generation of the correlation, the state being the state of the energy lower than the state in which the correlation is not generated. By the extended Kohn-Sham equation, it is possible to properly make the expression of the system by a certain state in which the correlation is generated.

Figure 9:
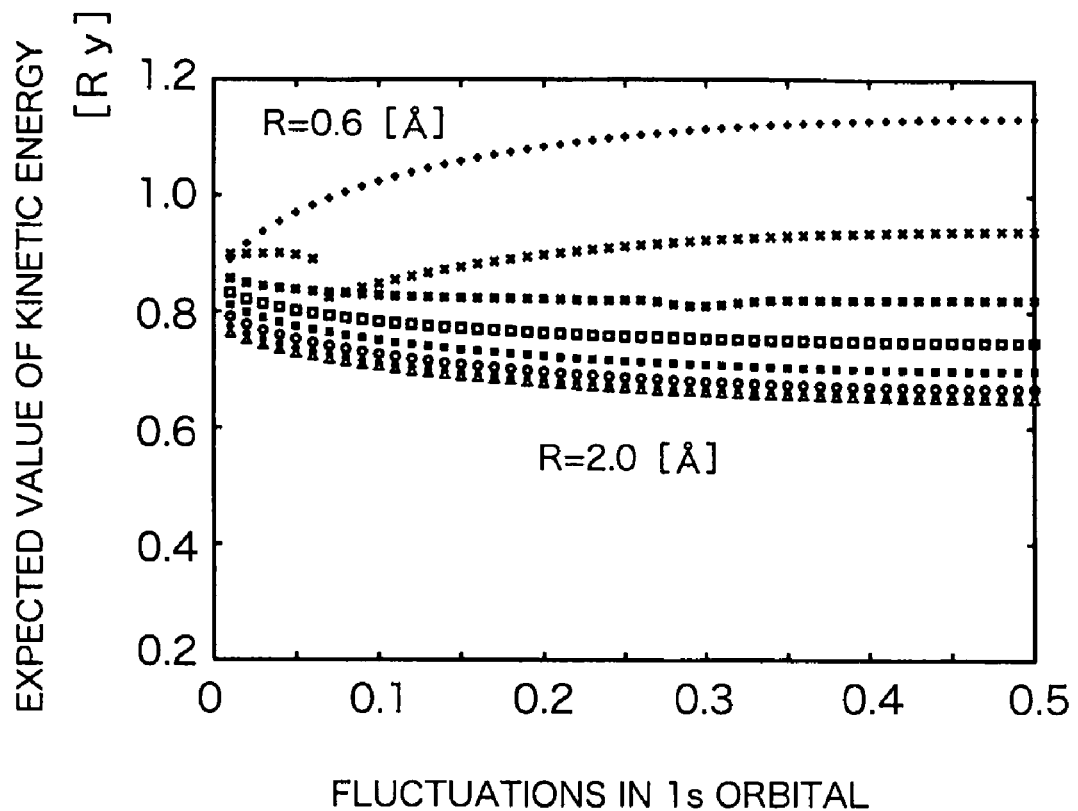
FIG. 9 is a graph illustrating a relation between fluctuations in 1s orbital in a hydrogen molecule and a kinetic energy.

Possibility of such a state is shown by the following calculation result of the extended Kohn-Sham equation regarding a hydrogen molecule. FIG. 9 is a graph illustrating a relation between the fluctuations and the kinetic energy in 1s orbital in the hydrogen molecule. The abscissa axis shows the magnitude of the fluctuations in the 1s orbital, and the longitudinal axis shows the expected value of the kinetic energy. This graph shows the change of the energy when an inter-atomic distance is changed from 0.6 Å to 2.0 Å by 0.2 Å with the symbols changed.

Figure 10:
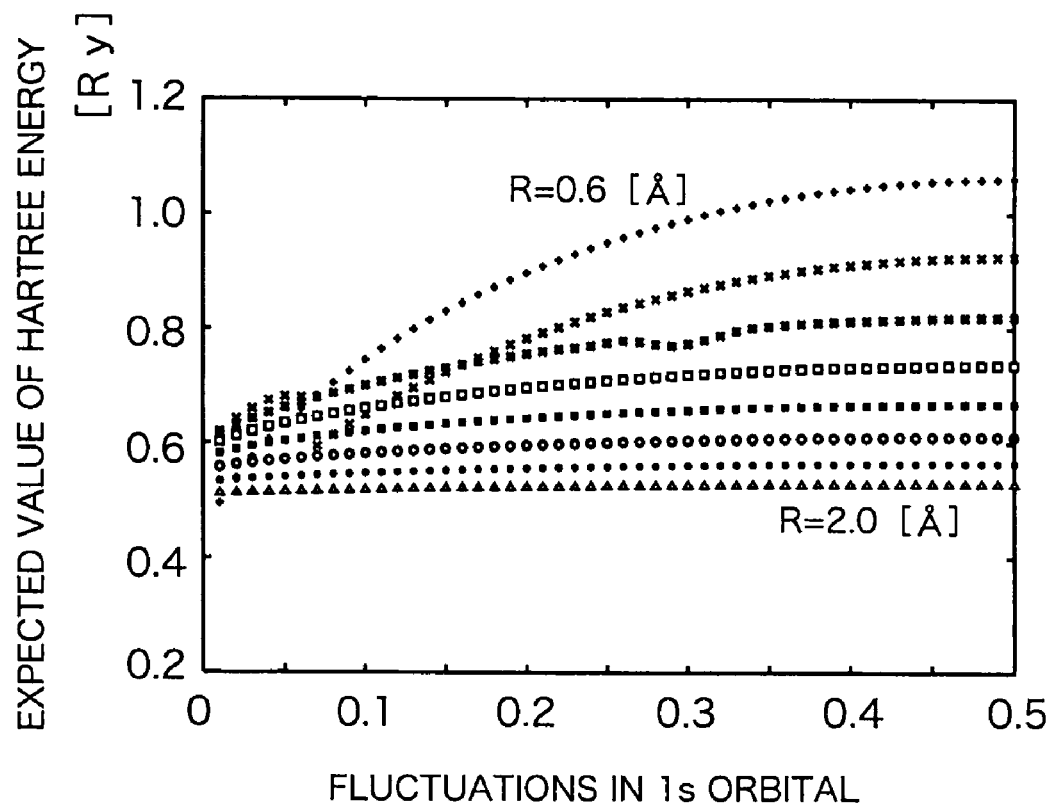
FIG. 10 is a graph illustrating a relation between fluctuations in 1s orbital in a hydrogen molecule and a Hartree energy.

In addition, FIG. 10 is a graph illustrating the relation between the fluctuations in the 1s orbital in the hydrogen molecule and the expected values of the Hartree energy. In the same way as the graph of FIG. 9, the abscissa axis shows the magnitude of the fluctuations in the 1s orbital, and the longitudinal axis shows the expected value of the Hartree energy, and this graph shows the change of the energy when the inter-atomic distance is changed from 0.6 Å to 2.0 Å by 0.2 Å with the symbols changed.

It is found from the graph of FIG. 10, that the Hartree energy is approximately constant irrespective of the fluctuations when the inter-atomic distance is set at 2.0 Å. In addition, it is found from the graph of FIG. 9 that the tendency of the relative value of the kinetic energy is reversed by the inter-atomic distance. That is, when the inter-atomic distance is short, the expected value of the kinetic energy becomes smaller as the fluctuations become smaller. Meanwhile, this tendency is reversed in the vicinity of 1.0 Å. in the inter-atomic distance, and the tendency of increasing the kinetic energy as the fluctuations become smaller is observed, and it is found that suppression of the fluctuations are generated.

Accordingly, by changing the magnitude of the fluctuations and calculating the expected value of the kinetic energy in the aforementioned equation 21, it is possible to determine whether or not the suppression of the fluctuations are generated. The electronic state calculation device 20 determines whether or not the suppression of the fluctuations are generated by performing the self-consistent calculation with the effective interaction of the equation 21 made variable (step S72). When it is so determined that the suppression of the fluctuations are generated (YES: S72), the evaluation of the physical quantities is performed by the extended Kohn-Sham theory (step S73), and when it is so determined that the suppression of the fluctuations are not generated (NO: S72), the evaluation of the physical quantities by the conventional Kohn-Sham theory is performed (step S74).

Thus, in this embodiment, a calculation procedure of the reference system by the highly accurate calculation technique such as the Quantum Monte Carlo method and the Configuration Interaction Method can be skipped, and therefore remarkable high speed calculation can be realized. In addition, this embodiment can be directly applied to a final target without requiring the reference system, and therefore can be directly applied to the calculation of a large-scale system. As a result, remarkable high accuracy can be achieved, and the description of the electronic state in the vicinity of a Fermi surface is possible, which is difficult conventionally. Further, in this embodiment, an evaluation method of the residual exchange correlation energy functional method is given, and therefore the highly accurate and high speed calculation method is realized as a practical calculation method surpassing the LDA, which has been a main approximation method in the density functional method, and capable of suppressing to a calculation procedure of virtually the same scale as the calculation step.

The invention claimed is:

1. An electronic state calculation method performed by an electronic state calculation device including a CPU connected to memory storage, the electronic state calculation method for calculating an electronic state of a substance by a first-principle calculation, comprising the steps of:

deciding a model to reproduce fluctuations of physical quantities characterizing physical properties of the substance using the electronic state calculation device; and obtaining the electronic state of the substance by the first-principle calculation with the decided model set as an initial condition using the electronic state calculation device, wherein the electronic state is obtained by using an optimization method based on an extended Kohn-Sham theory formulated by an expression including a residual exchange correlation energy functional expressed by the following equation:

$$E_{rxc}[n_\psi] = E_{xc}[n_\psi] + \min_{\Phi \to n_\Psi} \langle \Phi|T|\Phi \rangle - \min_{\Psi' \to n_\Psi} \langle \Psi'|T+V_{red}|\Psi' \rangle$$

wherein $n_\Psi$ indicates one-electron density, $E_{xc}[n_\Psi]$ indicates an exchange correlation energy functional, $\Phi$ indicates a many-particle wave function in a state in which correlation is not generated, $\Psi$ indicates a many-particle wave function in a state in which the correlation is generated, T indicates a kinetic energy operator, and $V_{red}$ indicates an operator defined by the following correlation function given by a set of physical quantities $\{X_i\}$:

$$\langle \Psi|V_{red}|\Psi \rangle = \sum_i W_i \langle \Psi|(X_i - \overline{X}_i) \cdot (X_i - \overline{X}_i)|\Psi \rangle$$

wherein i=1, 2, 3, . . . , N (N is the number of physical quantities to be calculated), $W_i$ indicates a parameter expressing a weight, and a symbol in a small parenthesis indicates a difference between the physical quantities $X_i$ and a mean value of the physical quantities X.

2. The electronic state calculation method according to claim 1, wherein by changing a magnitude of the fluctuations with effective interaction between electrons made variable, evaluation of a kinetic energy and a total energy is performed in two states of a state in which there are fluctuations to reproduce the same electron density and a state in which there are no fluctuations.

3. The electronic state calculation method according to claim 1, wherein when the model is decided, fluctuations with respect to the physical quantities are calculated by using a calculation technique of a many-body electron system, and fluctuations with respect to the physical quantities are calculated based on an extended Kohn-Sham theory including an exchange correlation potential and Coulomb interaction between electrons, and parameters describing the model are decided such that each component of a set of the fluctuations calculated by using the calculation technique of a many-body electron system and the corresponding component of a set of the fluctuations calculated based on the extended Kohn-Sham theory are approximately equal to each other.

4. The electronic state calculation method according to claim 3, wherein the extended Kohn-Sham theory is formulated as an optimization problem of a wave function functional expressed by the following equation:

$$G_{Wi}[\Psi] = \langle \Psi|T+V_{red}|\Psi \rangle - \min_{\Psi' \to n_\Psi} \langle \Psi'|T+V_{red}|\Psi' \rangle + F[n_\Psi] + \int d^3 r v_{ext}(r) n_\Psi(r)$$

wherein $\Psi$ indicates a many-particle wave function, T indicates a kinetic energy operator, $n_\Psi$, indicates one-electron density, F[n] indicates a universal energy functional, $\Psi'$ indicates a many-particle wave function minimizing $\langle T+V_{red} \rangle$ with a condition that one electron density $n_\Psi$ is reproduced, $v_{ext}$ indicates an external interaction potential, and $V_{red}$ indicates an operator defined by the equation $$\langle \Psi|V_{red}|\Psi \rangle = \sum_i W_i \langle \Psi|(X_i - \overline{X}_i) \cdot (X_i - \overline{X}_i)|\Psi \rangle.$$

5. The electronic state calculation method according to claim 4, wherein a plane wave basis expansion method, a reinforced plane wave basis expansion method, an actual space, a numerical basis expansion method, a mixed basis expansion method, a localized basis expansion method, or a linear MT orbital method are used for the calculation of a correlation function based on the extended Kohn-Sham theory.

6. The electronic state calculation method according to claim 3, wherein the parameter includes a parameter regarding an exchange correlation energy and local interaction between electrons.

7. The electronic state calculation method according to claim 3, wherein the calculation technique includes a Quantum Monte Carlo Method, a Transcorrelated Method, a Configuration Interaction Method, a Perturbational calculation/Green's function Method, or an Effective Potential Method.

8. The electronic state calculation method according to claim 1, wherein a plane wave basis expansion method, a reinforced plane wave basis expansion method, an actual space, a numerical basis expansion method, a mixed basis expansion method, a localized basis expansion method, or a linear MT orbital method are used for the calculation of a correlation function based on the extended Kohn-Sham theory.

9. The electronic state calculation method according to claim 1, wherein the fluctuations are described by two-dimensional correlation function having a positive definite and a bounded value range.

10. The electronic state calculation method according to claim 1, wherein the physical quantities are quantities described by numerical operators or generation/annihilation operators regarding electrons in a localized orbital.

11. The electronic state calculation method according to claim 1, wherein the physical quantities are physical quantities deciding a structural factor, an optical response coefficient, or a dielectric constant, magnetic permeability, electric conductivity, or elasticity of the substance.

12. An electronic state calculation device that calculates an electronic state of a substance by a first-principle calculation, comprising:
a processor which decides a model to reproduce fluctuations of physical quantities characterizing physical properties of the substance, and obtains the electronic state of the substance by the first-principle calculation with the decided model set as an initial condition,
wherein the electronic state is obtained by using an optimization technique based on an extended Kohn-Sham theory formulated by an expression including a residual exchange correlation energy functional expressed by the following equation:

$$E_{rxc}[n_\psi] = E_{xc}[n_\psi] + \min_{\Phi \to n_\Psi} \langle \Phi|T|\Phi \rangle - \min_{\Psi' \to n_\Psi} \langle \Psi'|T + V_{red}|\Psi' \rangle$$

wherein $n_\Psi$ indicates one-electron density, $E_{xc}[n_\Psi]$ indicates an exchange correlation energy functional, $\Phi$ indicates a many-particle wave function in a state in which correlation is not generated, $\Psi'$ indicates a many-particle wave function in a state in which the correlation is generated, T indicates a kinetic energy operator, and $V_{red}$ indicates an operator defined by the following correlation function given by a set of physical quantities $\{X_i\}$:

$$\langle \Psi|V_{red}|\Psi \rangle = \sum_i W_i \langle \Psi|(X_i - \overline{X}_i) \cdot (X_i - \overline{X}_i)|\Psi \rangle$$

wherein i=1, 2, 3, ..., N (N is the number of physical quantities to be calculated), $W_i$ indicates a parameter expressing a weight, and a symbol in a small parenthesis indicates a difference between the physical quantities $X_i$ and a mean value of the physical quantities $X_i$.

13. The electronic state calculation device according to claim 12, comprising: a processor for evaluating a kinetic energy and a total energy in two states of a state in which there are fluctuations to reproduce the same electron density and a state in which there are no fluctuations, by changing a magnitude of the fluctuations with effective interaction between electrons made variable.

14. The electronic state calculation device according to claim 12, comprising a processor for calculating fluctuations with respect to the physical quantities by using a calculation technique of a many-body electron system, means for calculating fluctuations with respect to the physical quantities based on an extended Kohn-Sham theory including an exchange correlation potential and Coulomb interaction between electrons, and means for deciding parameters describing the model such that each component of a set of the fluctuations calculated by using the calculation technique of a many-body electron system and the corresponding component of a set of fluctuations calculated based on the extended Kohn-Sham theory are approximately equal to each other.

15. The electronic state calculation device according to claim 14, wherein the extended Kohn-Sham theory is formulated as an optimization problem of a wave function functional expressed by the following equation:

$$G_{Wi}[\Psi] = \langle \Psi|T + V_{red}|\Psi \rangle - \min_{\Psi' \to n_\Psi} \langle \Psi'|T + V_{red}|\Psi' \rangle + F[n_\Psi] + \int d^3 r v_{ext}(r) n_\Psi(r)$$

wherein $\Psi$ indicates a many-particle wave function, T indicates a kinetic energy operator, $n_\Psi$ indicates one-electron density, F[n] indicates a universal energy functional, $\Psi'$ indicates a many-particle wave function minimizing $\langle T+V_{red} \rangle$ with a condition that one electron density $n_\Psi$ is reproduced, $v_{ext}$ indicates an external interaction potential, and $V_{red}$ indicates an operator defined by the equation $$\langle \Psi|V_{red}|\Psi \rangle = \sum_i W_i \langle \Psi|(X_i - \overline{X}_i) \cdot (X_i - \overline{X}_i)|\Psi \rangle.$$

16. A non-transitory computer-readable recording medium storing a computer program that causes a computer to calculate an electronic state of a substance by a first-principle calculation, the computer program causing the computer to execute the steps comprising:
regarding physical quantities characterizing physical properties of the substance, causing the computer to decide a model to reproduce fluctuations of the physical quantities; and
causing the computer to calculate an electronic state of the substance by the first-principle calculation with the decided model set as an initial condition, wherein an optimization technique is used, which is based on an extended Kohn-Sham theory formulated by an expression including a residual exchange correlation energy functional expressed by the following equation, as the first-principle calculation:

$$E_{rxc}[n_\psi] = E_{xc}[n_\psi] + \min_{\Phi \to n_\Psi} \langle \Phi|T|\Phi \rangle - \min_{\Psi' \to n_\Psi} \langle \Psi'|T + V_{red}|\Psi' \rangle$$

wherein $n_\Psi$ indicates one-electron density, $E_{xc}[n_\Psi]$ indicates an exchange correlation energy functional, $\Phi$ indicates a many-particle wave function in a state in which no correlation is generated, $\Psi'$ indicates the many-particle wave function in a state in which the correlation is generated, T indicates a kinetic energy operator, and $V_{red}$ indicates an operator defined by the following correlation function given by a set of physical quantities $\{X_i\}$:

$$\langle \Psi|V_{red}|\Psi \rangle = \sum_i W_i \langle \Psi|(X_i - \overline{X}_i) \cdot (X_i - \overline{X}_i)|\Psi \rangle$$

wherein i=1, 2, 3, ..., N (N is the number of the physical quantities to be calculated), $W_i$ indicates a parameter expressing a weight, and a symbol in a small parenthesis indicates a difference between the physical quantities $X_i$ and a mean value of the physical quantities $X_i$.

17. The recording medium according to claim 16, wherein an optimization technique based on an extended Kohn-Sham theory formulated by an expression including a wave function functional expressed by the following equation is used as the first-principle calculation:

$$G_{W_i}[\Psi] = \langle\Psi|T+V_{red}|\Psi\rangle - \min_{\Psi'\to n_\Psi}\langle\Psi'|T+V_{red}|\Psi'\rangle + F[n_\Psi] + \int d^3r\, v_{ext}(r)n_\Psi(r)$$

wherein $\Psi$ indicates a many-particle wave function, T indicates a kinetic energy operator, $n_\Psi$ indicates one-electron density, F[n] indicates a universal energy functional, $\Psi'$ indicates the many-particle wave function minimizing $\langle T+V_{red}\rangle$ with a condition that one electron density $n_{\Psi'}$ is reproduced, $v_{ext}$ indicates an external interaction potential, and $V_{red}$ indicates an operator defined by the equation $$\langle\Psi|V_{red}|\Psi\rangle = \sum_i W_i\langle\Psi|(X_i-\overline{X}_i)\cdot(X_i-\overline{X}_i)|\Psi\rangle.$$

* * * * *